US008506555B2

(12) United States Patent
Ruiz Morales

(10) Patent No.: US 8,506,555 B2
(45) Date of Patent: Aug. 13, 2013

(54) ROBOTIC SURGICAL SYSTEM FOR PERFORMING MINIMALLY INVASIVE MEDICAL PROCEDURES

(75) Inventor: Emilio Ruiz Morales, Taino (IT)

(73) Assignee: The European Atomic Energy Community (Euratom) (BE)

( * ) Notice: Subject to any disclaimer, the term of this patent is extended or adjusted under 35 U.S.C. 154(b) by 1303 days.

(21) Appl. No.: 12/162,902

(22) PCT Filed: Feb. 2, 2007

(86) PCT No.: PCT/EP2007/051047
§ 371 (c)(1),
(2), (4) Date: Jul. 31, 2008

(87) PCT Pub. No.: WO2007/088208
PCT Pub. Date: Aug. 9, 2007

(65) Prior Publication Data
US 2009/0024142 A1    Jan. 22, 2009

(30) Foreign Application Priority Data
Feb. 3, 2006    (EP) ................................ 06101251

(51) Int. Cl.
*A61B 19/00*    (2006.01)

(52) U.S. Cl.
USPC .......................... 606/1; 901/9; 901/14

(58) Field of Classification Search
None
See application file for complete search history.

(56) References Cited

U.S. PATENT DOCUMENTS 5,351,676 A    10/1994  Putman
5,795,387 A *  8/1998   Huerta ........................ 118/244
(Continued)

FOREIGN PATENT DOCUMENTS

JP    52022271         2/1977
JP    59146786  A      8/1984
(Continued)

OTHER PUBLICATIONS

JR3: "Sensors with Acceleration Compensation", XP002392369, [Online], Mar. 7, 2005.

(Continued)

*Primary Examiner* — Sam Yao
*Assistant Examiner* — Scott T Luan
(74) *Attorney, Agent, or Firm* — Cantor Colburn LLP

(57) ABSTRACT

A robotic surgical system for performing minimally invasive medical procedures includes a robot manipulator for robotically assisted handling of a laparoscopic instrument having a manipulator arm, a manipulator wrist supported by the arm and an effector unit supported by the wrist, wherein the manipulator arm provides three degrees-of-freedom by means of a first joint, a second joint and a third joint, each having an associated actuator, for robotically positioning the wrist, the wrist providing two degrees-of-freedom by means of a fourth joint and a fifth revolute joint having an associated actuator, for robotically setting the yaw angle and the pitch angle of the effector unit respectively; the effector unit includes a laparoscopic instrument actuator and provides one degree-of-freedom by means of a revolute sixth joint having an associated actuator for robotically setting the roll angle of the LIA which includes a seat, with an associated coupling mechanism for mounting an instrument stem adaptor to the effector unit, and an actuation mechanism cooperating with the instrument stem adaptor for actuating a laparoscopic instrument connected to the adaptor. The effector unit is configured such that the rotation axis of the revolute sixth joint coincides with the longitudinal axis of a laparoscopic instrument mounted to the effector unit and the effector unit includes a sensor assembly having a 6 degree-of-freedom (DOF) force/torque sensor and a 6 DOF accelerometer. The sensor assembly connects the LIA to the sixth revolute joint.

25 Claims, 27 Drawing Sheets

(56) References Cited

U.S. PATENT DOCUMENTS

| | | |
|---|---|---|
| 6,436,107 B1 | 8/2002 | Wang et al. |
| 6,539,083 B1 * | 3/2003 | Churchman ............ 379/146 |
| 6,645,196 B1 * | 11/2003 | Nixon et al. ............ 606/1 |
| 6,659,939 B2 | 12/2003 | Moll et al. |
| 2002/0032452 A1 | 3/2002 | Tierney |
| 2005/0021050 A1 | 1/2005 | Cooper |
| 2005/0222554 A1 | 10/2005 | Wallace |
| 2006/0107775 A1 * | 5/2006 | Wright et al. ............ 73/866.5 |
| 2008/0004632 A1 * | 1/2008 | Sutherland et al. ............ 606/130 |

FOREIGN PATENT DOCUMENTS

| | | |
|---|---|---|
| JP | 09141589 | 6/1997 |
| WO | 9700649 A1 | 1/1997 |

OTHER PUBLICATIONS

Japanese Office Action P2008-552824; Dated Sep. 21, 2011.

* cited by examiner

ROBOTIC SURGICAL SYSTEM FOR PERFORMING MINIMALLY INVASIVE MEDICAL PROCEDURES

TECHNICAL FIELD OF THE INVENTION

The claimed invention relates to the field of medical equipment and more particularly to a robotic surgical system for performing minimally invasive medical procedures, in particular laparoscopic procedures.

BRIEF DISCUSSION OF RELATED ART

It is well known that, as opposed to laparotomy, minimally invasive medical procedures have the benefit of reducing the amount of extraneous tissue that is damaged during diagnostic or surgical procedures. This results in shorter patient recovery time, less discomfort and deleterious side effects, and lower costs of the hospital stay. Nowadays, in general surgery, urology, gynaecology and cardiology specialties, there is an increase of the amount of surgical operations carried out by minimally invasive techniques, such as laparoscopic techniques.

Minimally invasive techniques in general and laparoscopy in particular do however put more stringent requirements on the surgeon carrying out the operation. The surgeon operates in an uncomfortable and tiring posture, with a limited field of view, reduced freedom of motion and poor tactile perception. To these problems adds the fact that surgeons often have to carry out several consecutive interventions per day, each intervention lasting e.g. from 30 minutes to several hours. In spite of these difficulties, the trend towards minimally invasive procedures is probably going to increase sharply in the coming years due to the ageing population and the pressure of costs in the medical field.

In laparoscopy the surgeon is obviously required to be as precise in his moves as in laparotomy. Manipulating long-shaft instruments with freedom of motion reduced to four degrees of freedom about a fulcrum at the instrument access port, i.e. at the incision in the patient body, is not alleviating this task. Complications arise inter alia by the fact that the required posture is quite tiresome and reduces the already limited perception of interacting forces between instrument and tissues. For example, when the surgeon stands aside the patient, he must lift and maintain stretched one of his arms to hold the instrument inserted at the opposite side of the patient. As a result, motorial capabilities of the surgeon decay normally after 20-30 minutes, such that among others trembling, loss of accuracy and loss of tactile sensitivity occur with the resulting risks for the patient. Therefore, new technologies, such as robotically assisted laparoscopy, are emerging which aim at improving efficiency, quality and safety of interventions.

In view of the above, robotically assisted laparoscopy has known significant development since the early nineties. Two representative commercially available robotic surgery systems are the surgery system known by the trademark 'DA VINCI' developed by Intuitive Surgical Inc., Sunnyvale, Calif. and the surgery system known by the trademark 'ZEUS' originally developed by Computer Motion Inc., Goleta, Calif. The surgery system known by the name 'DA VINCI' is described among others by Moll et al. in U.S. Pat. Nos. 6,659,939; 6,837,883 and other patent documents of the same assignee. The surgery system known by the name 'ZEUS' is described among others by Wang et al. in U.S. Pat. Nos. 6,102,850; 5,855,583; 5,762,458; 5,515,478 and other patent documents assigned to Computer Motion Inc., Goleta, Calif.

These tele-operated robotic systems permit to control surgical interventions either directly from the operation theatre or from a remote site, using visual feed-back on a console. In either case, the tiring posture of the surgeon is eliminated.

Both these systems are designed specifically for cardiologic surgery where the topological anatomy is constant, the workspace is small and, therefore, accurate instrument motion and dexterity are required in a limited space only. In order to increase reachability and dexterity in this limited space, a vast range of special dedicated instruments, which provide one or more additional degrees of freedom at the instrument tip, have been designed for use with each of these systems respectively. Regarding these dedicated complex instruments, their high purchase cost and short lifetime due to sterilization increase the overall maintenance expenses. According to experienced surgeons in laparoscopy, articulated instruments are not essential for most procedures and the use of standard instruments would represent, among others, a significant reduction of maintenance costs.

BRIEF SUMMARY OF THE INVENTION

Accordingly, to the invention provides a robotic surgical system for performing minimally invasive medical procedures comprising a robot manipulator, which is configured such that it allows the use of available standard laparoscopic instruments that were designed for conventional manual procedures.

The invention more particularly provides a robotic surgical system for performing minimally invasive medical procedures comprising a robot manipulator for robotically assisted handling of a laparoscopic instrument, the robot manipulator having a manipulator arm, a manipulator wrist supported by the manipulator arm and an effector unit supported by the manipulator wrist, as disclosed hereinafter is proposed. According to one aspect of the invention, the manipulator arm provides three degrees-of-freedom by means of a first joint, a second joint and a third joint, each having an associated actuator, for robotically positioning the wrist. The manipulator wrist provides two degrees-of-freedom by means of a fourth joint and a fifth joint, the fourth and fifth joints being revolute joints and having an associated actuator, for robotically setting, with respect to the manipulator arm, the yaw angle and the pitch angle of the effector unit respectively. The effector unit comprises a laparoscopic instrument actuator and provides one degree-of-freedom by means of a revolute sixth joint having an associated actuator for robotically setting the roll angle of the laparoscopic instrument actuator. In other words, the actuated sixth revolute joint allows rotating not only the instrument but also the whole instrument actuator part of the effector unit. Furthermore, according to another aspect of the invention, the laparoscopic instrument actuator comprises a seat, with an associated coupling or locking mechanism for mounting an instrument stem adaptor to the effector unit, and a actuation mechanism cooperating with the instrument stem adaptor for actuating a laparoscopic instrument connected to the adaptor, preferably by linear actuation. The effector unit is configured such that the rotation axis of the revolute sixth joint coincides with the longitudinal axis of a laparoscopic instrument mounted to the effector unit by means of the instrument stem adaptor and the effector unit comprises a sensor assembly including a 6 degree-of-freedom (DOF) force/torque sensor and a 6 DOF accelerometer. The sensor assembly mechanically connects the laparoscopic instrument actuator to the sixth revolute joint. In other words, the sensor assembly is arranged in between the laparoscopic instrument actuator and the drive side of the sixth revolute joint such that it rotates with the laparoscopic instrument actuator. This enables inter alia a manual operation mode where the whole laparoscopic instrument actuator can be positioned and oriented manually using the sensor assembly as an input device controlling actuation of the six joints of the robot manipulator.

By virtue of the robotically actuated 6 DOF for manipulating the instrument, the robot manipulator provides, at the mounted laparoscopic instrument, a level of manoeuvrability comparable to that of a surgeon's hand without requiring any redundant joints. With the seat and coupling mechanism designed for an instrument stem adaptor, the laparoscopic instrument actuator provides a generic interface for a wide variety of existing standard type laparoscopic instruments designed for manual laparoscopy. Furthermore, the sensor assembly, arranged between the connected instrument and the sixth joint of the robot manipulator, enables accurate force feedback at a haptic interface on a surgeon console in order to provide the surgeon with a sensorial perception corresponding to manual handling of the instruments. It will be appreciated that the linear and angular accelerometer is used for compensating gravitational and acceleration influence on the force-torque sensor. These features enable the use of comparatively inexpensive standard type instruments (e.g. graspers, dissectors, scissors, coagulators, clips appliers, needle carriers, electro-bistouries, suction/irrigation tools, etc.) on the robot manipulator disclosed herein.

It will be appreciated that the system provides the required manoeuvrability with a minimum number of joints, i.e. with 6 DOF with only 6 joints. No further redundant joints are provided for motion of the manipulator. In particular, special instruments with articulated instrument distal ends are not required. Furthermore, all joints are actuated that is to say no passive (not actuated) or free-rotating joints are present in the robot manipulator, whereby robotic control is significantly improved. Elimination of redundant passive joints, which are commonly used in known systems e.g. for avoiding trocar stress, is achieved among others by providing the sensor assembly at the interface between the sixth joint and the laparoscopic instrument actuator. This arrangement of the sensor assembly enables force measurement and constraint restriction not only at the instrument tip level but also at the level of the trocar. Another particularity is to be seen in the fact that the wrist and effector unit joints are all rotary, i.e. no prismatic joints are provided on these parts.

Many existing robotic surgical systems lack force feedback and thereby preclude the surgeon from perception of forces exerted on the patient tissues. Hence, the surgeon can only rely on the visual feedback of his moves to limit the interaction of the instrument with the tissues. In fact, force feed-back significantly contributes to safety in the use of robotics for surgical laparoscopy. In addition, tactile sensing is relevant for palpating organs, for holding viscous organs with an instrument which is not in the field of view of the endoscope, for applying adequate tension to sutures and avoiding wire rupture, for detecting excessive forces applied to organs and consequently stopping or limiting motion, for limiting the forces applied on the trocar incision, etc. In "Development of actuated and sensor integrated forceps for minimally invasive robotic surgery" by B. Kübler, U. Seibold, and G. Hirzinger—Jahrestagung der Deutschen Gesellschaft für Computer—und Roboterassistierte Chirurgie (CURAC), Oct. 8-9, 2004, Munich, Germany; a miniaturized 6 DOF force/torque sensor installed at the tip of the instrument has been presented. This concept has several drawbacks, among which increased instrument expenses, the lack of robustness regarding sterilization, and EMI shielding problems when used with electrically powered instruments. Another issue, that cannot be addressed by sensors installed on the instrument stem, is the measurement of external forces applied to the trocar forming the instrument access port at the incision in the patient. In fact, these forces wear the incision and may loosen the trocar attachment. Hence sometimes the trocar is unintentionally pulled out from the incision during the intervention. It is well known that such an accident provokes, besides harm to the patient's tissue, a loss of abdominal insufflation pressure and thereby increases the intervention time since the situation must be recovered. By virtue of the force/torque sensor on the effector unit, automated procedures for avoiding trocar detachment can be implemented.

In the article "Towards robotic heart surgery: Introduction of autonomuous procedures into an experimental surgical telemanipulator system" by R. Bauernschmitt, E. U. Schirmbeck et al.—Int. J. Medical Robotics and Computer assisted Surgery, September 2005 (available from www.roboticpublications.com), the authors recognise the lack of force sensing and force feedback capabilities as a major drawback of currently available systems. The system described in this article comprises an industrial robot to which an instrument from Intuitive Surgical Inc., which was designed for the "DA VINCI" system, is mounted. In order to provide force sensing, the instrument is modified. It is equipped with strain gauge sensors on the instrument shaft near the distal end. This system, in contrast to the presently disclosed system, allows force measurement in the plane perpendicular to the instrument shaft only and requires the use of expensive dedicated instruments that were designed for robotic systems and provide three additional degrees of freedom at the distal end.

Another relevant aspect is versatility of the robotic surgery system. Existing robotic surgical systems are generally designed for a specific type of intervention. The "DA VINCI" and "ZEUS" systems, for example, were designed especially for cardiologic surgery. Therefore, as mentioned above, these systems are designed for special articulated instruments. Furthermore, because of the limited workspace in cardiologic interventions, instrument motion is normally downscaled from the surgeon's commands at haptic interface in these systems. In general laparoscopic surgery (including gynaecology and urology) the operating workspace is larger than in cardiology, the anatomical topology is variable (even sometimes unpredictable), and the mechanical properties of tissues and organs are diverse. Larger workspace implies a larger instrument motion envelope and the need of 1:1 motion scale. As a result, in general laparoscopy, increased motion dynamics are needed in order to accurately follow the surgeon hand motion. From experimental trials it has been found that the surgeon hand produces high speeds in a small workspace, and therefore very high acceleration. Speed can reach up to 100°/s along pivot pitch and yaw axes, and 200 mm/s in the penetration direction. At 1:1 motion scale and in the mentioned conditions, the above systems display vibrations, oscillations and loss of accuracy. The robot manipulator, described in more detail herein below, is designed to reduce such problems and hence to be suitable for a variety of interventions.

Another drawback related to special articulated laparoscopic instruments is that teleoperation based on the control of the articulated instrument tip revealed to be less intuitive than expected for experienced laparoscopic surgeons.

Many existing systems have, besides a manipulator for the endoscope, only two manipulators for surgical instruments per se. This results in increased intervention time due to frequent and complex instrument exchange procedures. In a typical intervention, the surgeon uses five to seven different types of instruments and often needs to exchange them several tenths of times. Usually, instrument exchange takes from 5 to 10 seconds, depending on the surgeon assistant's skill, and these exchange operations substantially contribute to the total intervention time (by approximately 10-20%). Many existing robotics systems are not readily suitable for typical interventions requiring three or four instrument access ports. Other systems are restricted to diagnostics interventions which are normally short in time (about 20 minutes) and often do not justify the cost of a robotics system. Ideally, a robotic surgery system should be modular and have the capability to manage up to four instrument access ports and one endoscope access port. A significant constraint, related to the design of suitable manipulators, is that some access ports can be distant by a few centimeters only and the respective instruments may need to be positioned nearly parallel or one above the other. In addition, it is desirable that manipulators do not excessively limit the surgeon's view on the patient body and access ports. The robotic surgical system, by virtue of various other features described herein below and considered inventive per se, addresses among others the latter issues.

In a preferred embodiment of the robot manipulator, the effector unit is configured such that one sensor axis, e.g. the normal axis, of the 6 DOF force/torque sensor and one sensor axis, e.g. the normal axis, of the 6 DOF accelerometer coincide with the rotation axis of the sixth joint. This measures facilitate force feedback calculations.

Preferably, when the laparoscopic instrument actuator comprises a housing with an access surface in which the seat is arranged and an interface flange which attaches the housing to the sensor assembly, it furthermore comprises gradual reinforcing ribs connecting the access surface to the interface flange for reinforcing the rigidity of attachment of the housing to the interface flange. Thereby, torques and forces are transmitted more accurately to the sensor assembly even if the cross-section of the laparoscopic instrument actuator is much smaller that that of the sensor mounting plate.

For increased ergonomics, the housing is semi-cylindrical by having a substantially semi-cylindrical surface opposite to the preferably substantially flat access surface. The semi-cylindrical surface is preferably in conformity with a cylindrical envelope of 50-135 mm, preferably of about 90 mm diameter and coaxial to the rotation axis of the sixth joint. In such embodiment it is further preferred that, the housing, the flange, the reinforcing ribs and the sensor assembly are dimensioned to fit into this cylindrical envelope. In addition the instrument step adapted is preferably designed to fit into the same envelope when mounted to the manipulator.

In a preferred configuration, the seat of the laparoscopic instrument actuator comprises an elongated essentially semi-cylindrical recess arranged, essentially coaxial to the axis of rotation of the sixth joint, in an access surface of the laparoscopic instrument actuator, the seat and the coupling or locking mechanism being configured for mounting and removing an instrument stem adaptor by a pivoting movement about the fulcrum in a plane that is essentially perpendicular to the instrument stem, i.e. in radial direction with respect to the axis of rotation of the sixth joint. The semi-cylindrical recess provides self-centering of the adaptor when the latter is connected. Furthermore, this configuration, combined with the ability to manually actuate the revolute sixth joint and, in normal conditions, combined with an automated procedure for moving the instrument near the access port, enables sideways installation and removal of the instrument and thereby eliminates insertion and extraction movements in the penetration direction with respect to the patient. Furthermore, ergonomics are improved for the surgeon assistant and instrument exchange times are reduced compared to known systems.

In a preferred embodiment of the coupling mechanism, the latter comprises at least one magnetic device, e.g. an electromagnet or permanent magnet or a combination of both, respectively arranged on either side of the semi-cylindrical recess. The magnetic devices, preferably provided in and level to the access surface, enable fastening an instrument stem adaptor to the laparoscopic instrument actuator by means of magnetic attraction. This coupling mechanism reduces the risk of damage to a sterile wrap covering the laparoscopic instrument actuator during interventions, since the latter need not be sterilized in this case.

In another simple and reliable embodiment enabling sideways mounting and removal of instruments, the seat comprises a longitudinal groove deepening the semi-cylindrical recess radially for receiving a coupling means arranged laterally on an instrument stem adaptor and wherein the coupling mechanism is configured as latch locking mechanism comprising a slideable catch arranged in the longitudinal groove for engaging the coupling means. This type of seat and locking mechanism, in cooperation with corresponding adaptors, provides a mechanically simple, intuitive and reliable quickcoupling connection.

Advantageously, the actuation mechanism, used for actuated instruments such as grasping or dissecting forceps, scissors, etc., comprises a slider carriage configured for engagingly receiving and for linearly sliding a slider pin of an instrument stem adaptor mounted to the effector unit. In case the seat is elongated along the rotation axis of the sixth joint, the slider carriage is preferably arranged laterally to the seat, i.e. to the side of the seat as opposed to in axial prolongation. Thereby, a length reduction of the effector unit can be achieved. Furthermore, the actuation mechanism advantageously comprises a force sensor, which connects the slider carriage to a driving means. Such a force sensor allows measuring forces exerted by or onto the slider carriage.

In a preferred embodiment, the laparoscopic instrument actuator further comprises a presence detector for detecting whether an instrument stem adaptor is correctly mounted to the effector unit. Preferably, the laparoscopic instrument actuator comprises a plurality of inductive presence sensors for identifying an instrument mounted to the effector unit by means of an inductively identifiable material pattern provided on the instrument stem adaptor.

In a preferred embodiment, the robotic surgical system is configured for operating in a manual mode, in which the laparoscopic instrument actuator can be positioned and oriented by the robot manipulator using information read by the 6 DOF force/torque sensor of the sensor assembly, and further comprises switching means arranged on the laparoscopic instrument actuator for switching the system to this manual mode.

Another aspect of the claimed invention concerns the aforementioned laparoscopic instrument stem adaptor for mounting a stem of any available manual laparoscopic instrument to a robot manipulator in a robot surgical system as described herein. This adaptor comprises an elongated case having a stem connector arranged on a front end and a coupling member or means arranged laterally on the case. The stem connector cooperates with a socket of the stem of a manual laparoscopic instrument and is configured for detachable connection thereto. The coupling means in turn cooperate(s) with the seat of the laparoscopic instrument actuator of the robot manipulator.

For manual interventions, many different laparoscopic instruments are available for a variety of uses. Most of these instruments can be separated into a handle portion, which is conceived to be manipulated by a surgeon, and a stem portion, i.e. the elongated laparoscopic tube or shaft with the instrument per se on one end an a socket connecting to the handle on the opposite end. Provided with a corresponding connector, an adaptor as disclosed herein allows the use of any type of stem portion of such instruments on a robot manipulator as described above. The adaptor has a very simple inexpensive and robust design. Hence, combined with standard comparatively inexpensive instruments, the instrument stem adaptor reduces purchase and maintenance cost of the medical tools to be used in combination the above robotic system.

In a preferred embodiment of the stem adaptor, its coupling means comprise(s) a semi-cylindrical surface or, alternatively, the entire case can have an essentially cylindrical shape, possibly, with a rounded end opposite the stem connector. In both cases, the shape or surface is conformed to the aforementioned semi-cylindrical recess of the seat in the laparoscopic instrument actuator of the robot manipulator. This allows centering the instrument stem adaptor on the rotation axis of the sixth joint.

For laparoscopic instruments with an actuating rod, e.g. grasping or dissecting forceps, scissors, etc., the laparoscopic instrument stem adaptor, preferably comprises an internal cylindrical hollow as a guide for a piston of a manual laparoscopic instrument, which can be arranged to slide in the guide. It further preferably comprises a through hole for a slider pin attached transversely to the piston and protruding from the case for operating the piston. The slider pin is configured to engage a slider carriage of the laparoscopic instrument actuator and the piston cooperates with an internal actuating rod of a laparoscopic instrument connected to the adaptor for operating the tool at the tip of the laparoscopic instrument. This configuration of the adaptor and the corresponding laparoscopic instrument actuator provides simple and reliable motion transmission and furthermore eliminates additional manual steps for establishing motion transmission when installing or removing an instrument on the effector unit. By virtue of the design of the adaptor and the corresponding coupling on the robot manipulator, instrument exchange time is reduced which contributes to reducing overall intervention time.

For fastening the instrument stem adaptor to the laparoscopic instrument actuator by means of magnetic attraction produced by the magnetic devices, it is preferable that the coupling means comprises at least one ferromagnetic element arranged on either side of the case, the ferromagnetic elements cooperating respectively with a corresponding magnetic device of the coupling mechanism on the laparoscopic instrument actuator. In this embodiment, the instrument stem adaptor preferably further comprises a lever for detaching the adaptor from the laparoscopic instrument actuator.

In order to allow identification of an instrument using the aforementioned inductive presence sensors, the adaptor may comprise an inductively identifiable pattern provided on the instrument stem. Furthermore, the adaptor may comprise an electrical connector arranged opposite to said coupling means for transmitting electric power to an instrument connected to said stem connector.

BRIEF DESCRIPTION OF THE FIGURES

The above aspects as well as other inventive aspects of the present disclosure will be more apparent from the following description of a not limiting embodiment with reference to the attached drawings, wherein.

In these drawings identical reference numerals are used to identify identical parts throughout.

DETAILED DESCRIPTION OF THE INVENTION

Figure 1:
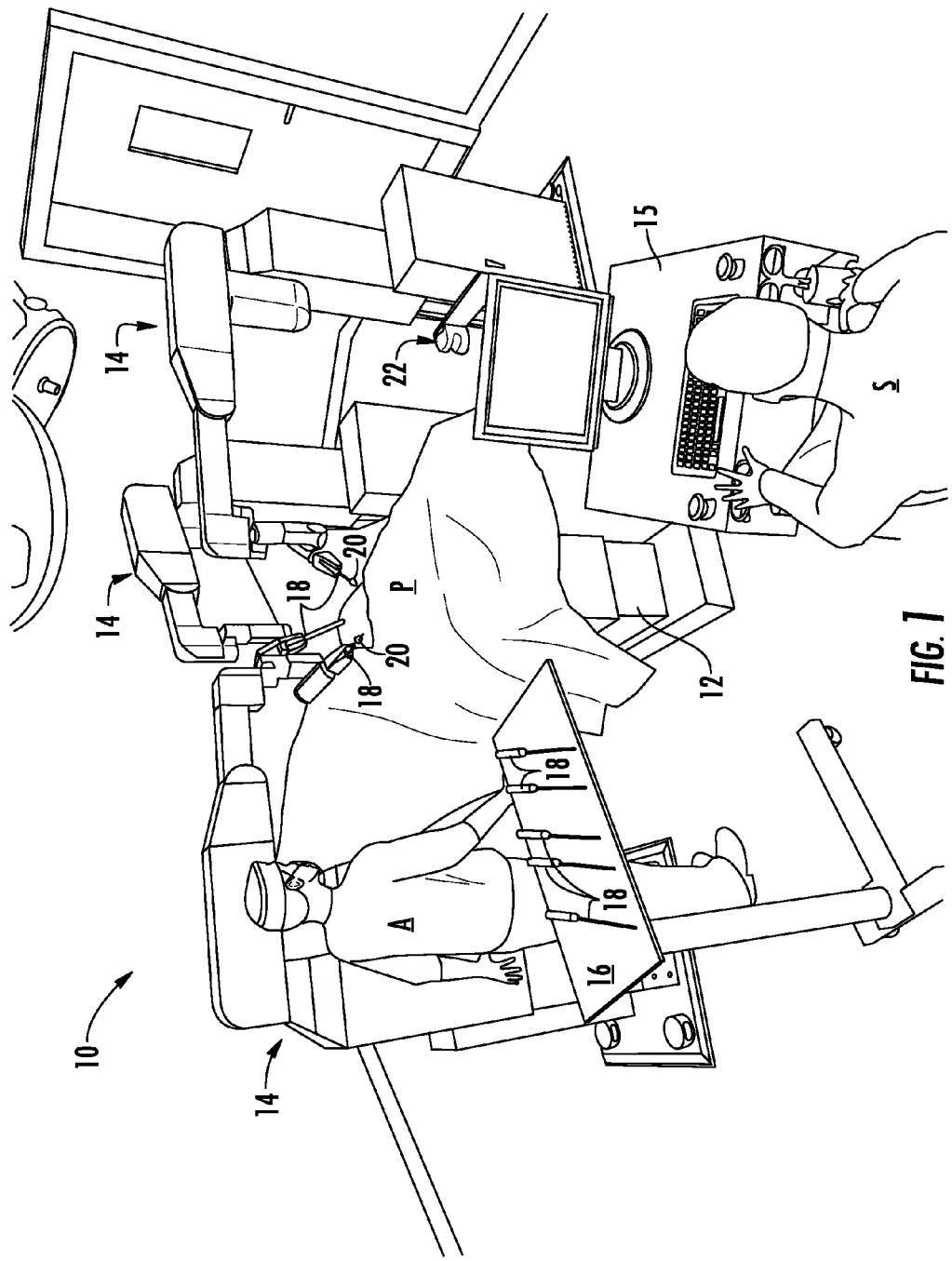
FIG. 1: is a perspective view of a robotic surgical system for generic surgical laparoscopy in an operation theatre with three robot manipulators placed around an operation table on which lays a patient.
Figure 3:
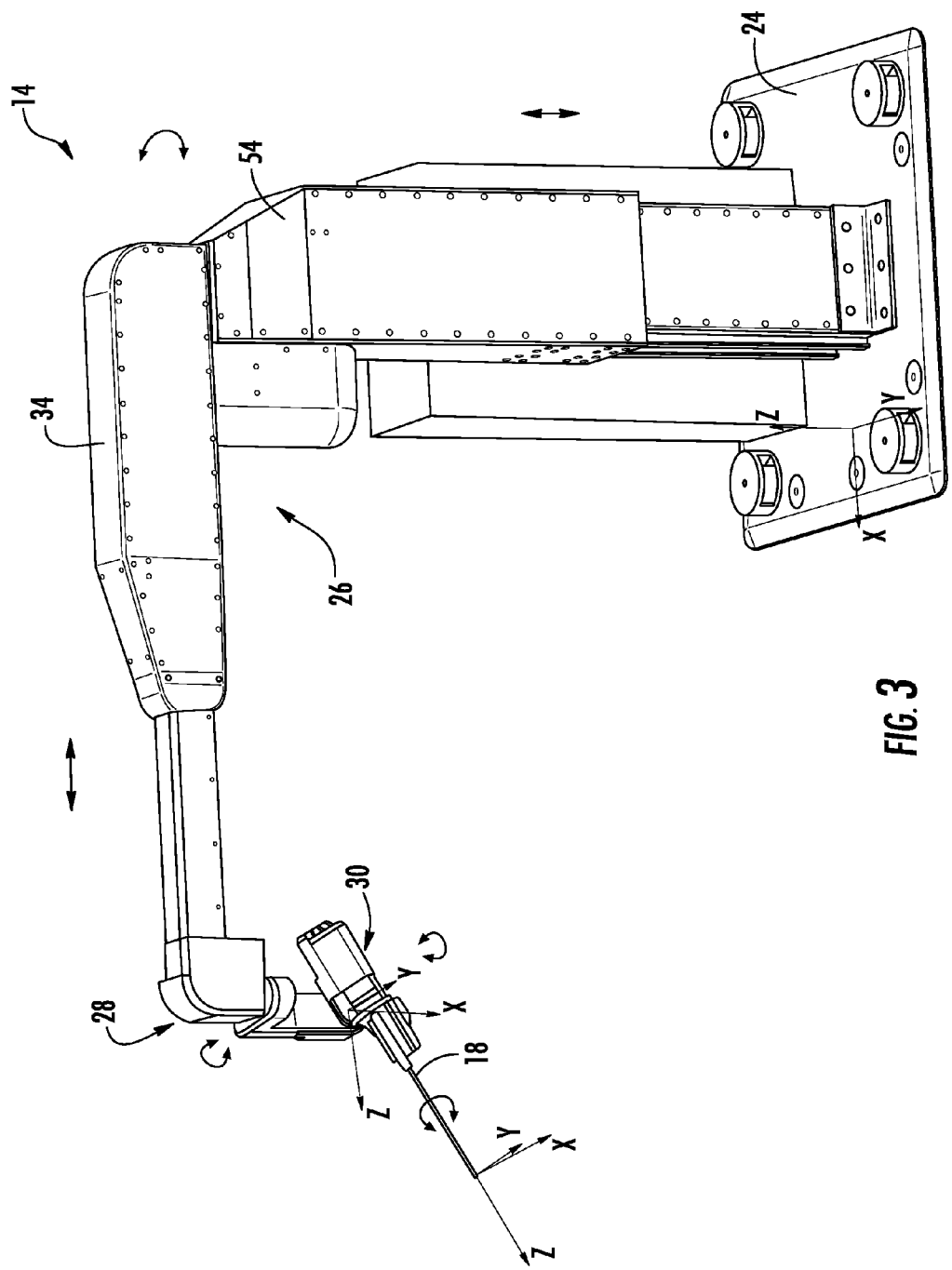
FIG. 3: is a perspective view of a robot manipulator of the robotic surgical system of FIG. 1 and FIG. 2 showing main coordinate systems.
Figure 4:
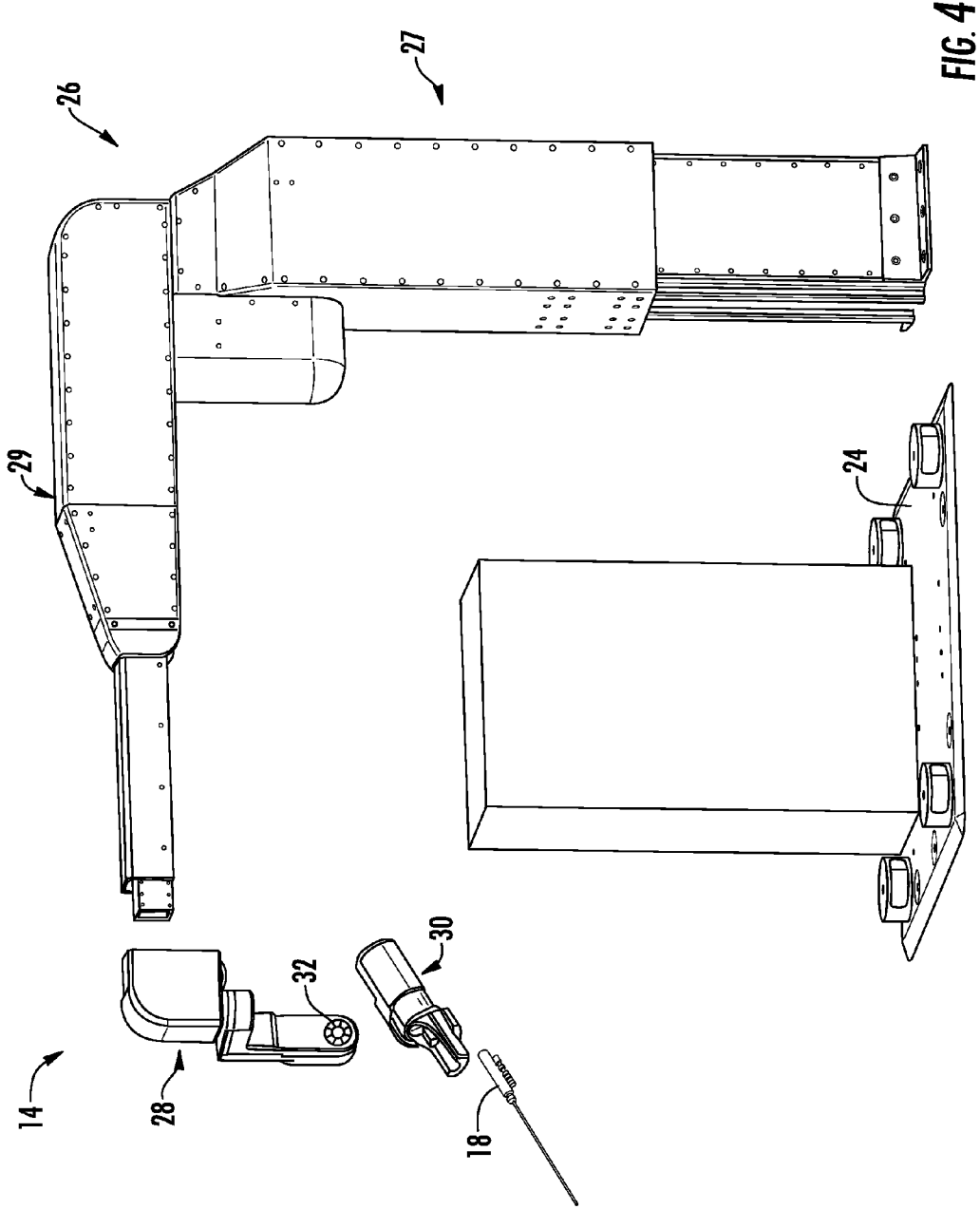
FIG. 4: is a perspective view of the robot manipulator of FIG. 3 partially disassembled into its main parts.

FIG. 1 shows a robotic surgical system for generic surgical laparoscopy, generally identified by reference numeral 10. A patient P covered by a sterile sheet is lying on an operation table 12 around which a plurality of robot manipulators 14 are disposed. In the example of FIG. 1, the robotic surgical system 10 is set up for an intervention on the pelvic area. A surgeon S operates a surgical master console 15 and a surgeon assistant A stands near the operation table 12 and near a tray 16 with a set of adapted laparoscopic instruments 18. The robot manipulators 14 are designed for positioning and orienting an effector unit which supports and possibly actuates various kinds of laparoscopic instruments 18. During operation, the robot manipulators 14 are tele-operated by one or more surgeons S via one or more surgical master consoles 15 which are connected to a control unit (not shown). As will be appreciated, the robotic surgical system 10 is modular and configurable according to the type of the surgical intervention, generally with up to 5 manipulators and normally a minimum configuration of 2 manipulators. A configuration of a robotic surgical system 10' with 5 manipulators 14 is shown for example in FIG. 2. The system 10 shown in FIG. 1 is equipped with laser range scanners 22 located at the base of each robot manipulator 14. The laser range scanners 22 are used for surgical assistant personnel safety in the operation theatre. FIG. 3 is a three-dimensional view of a robot manipulator 14 which forms one mechanical unit of the robotic surgery system 10. The robot manipulator 14 is mounted on a base 24, which is attachable to the floor of the operation theatre and mobile when not attached. Three coordinate systems are also shown in FIG. 3, i.e. the Base, Tool Flange (TF) and Laparoscopic Instrument Tip (LIT) coordinate system. As seen in FIG. 3, the robot manipulator 14 comprises a manipulator arm 26 and a manipulator wrist 28. In FIG. 4, the main parts of the robot manipulator 14 are shown. The arm 26 has an essentially vertical part 27 and an essentially horizontal part 29. The first end of the arm 26 on the vertical part 27 is to be attached to the base 24 whereas the wrist 28 is to be attached to the second end of the arm 26, i.e. the extremity of the horizontal part 29. An effector unit 30 for adapted laparoscopic instruments 18 is to be connected to a tool flange 32 of the wrist 28. As indicated by arrows in FIG. 3, the arm 26 has three degrees of freedom (DOF) and the wrist 28 has two DOF. Accordingly, the robot manipulator 14 is basically a 5 DOF robot manipulator. An auxiliary DOF for rotating the laparoscopic instrument 18 mounted to the effector unit 30 about its longitudinal axis is provided by the effector unit 30. The arrangement of the DOF of the robot manipulator 14 and the effector unit 30 will become more apparent from the following description of FIG. 5.

Figure 5:
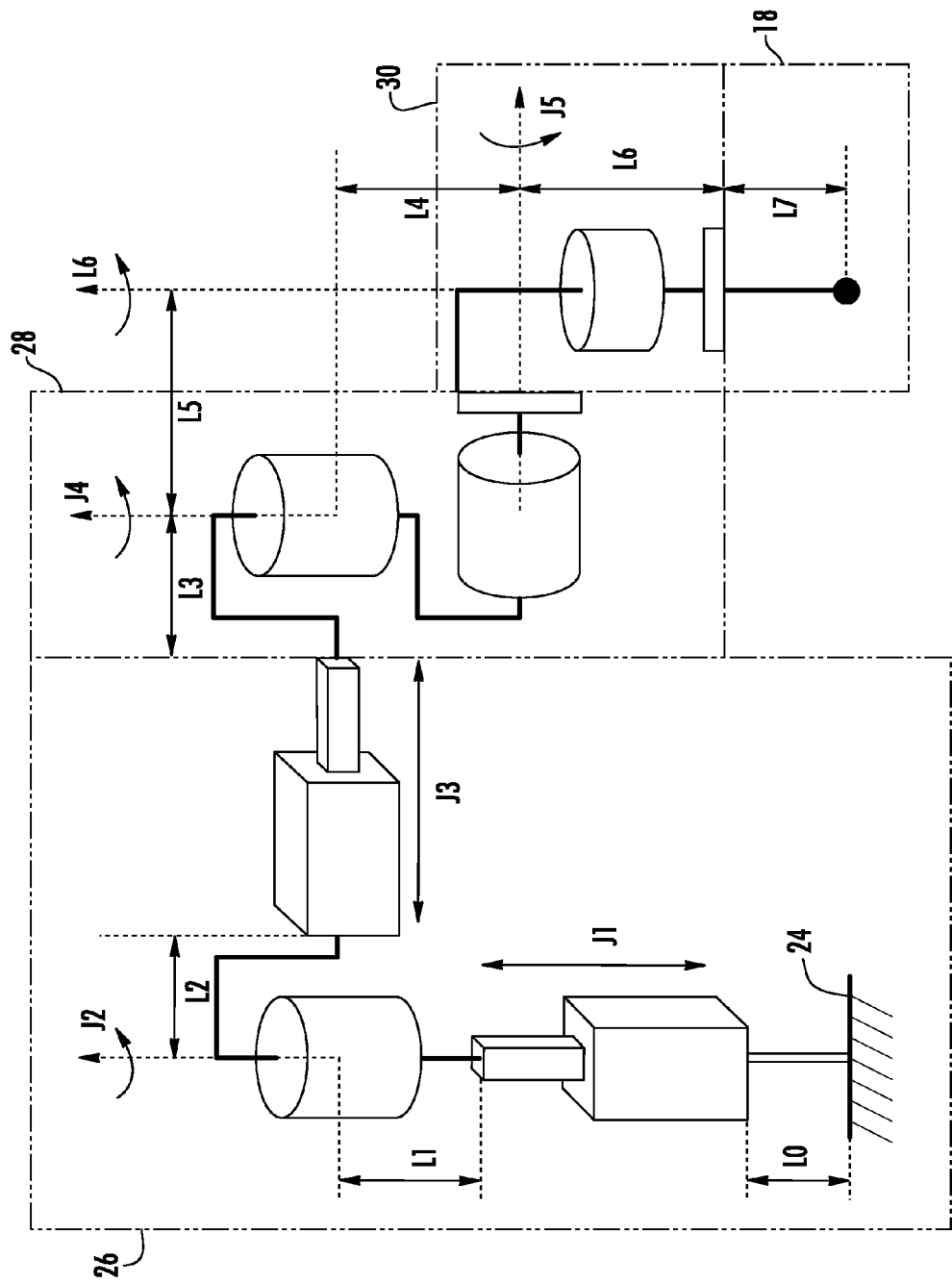
FIG. 5 is a schematic diagram of the kinematic configuration of the robot manipulator of FIG. 3 including joints J1 to J6.

As best seen in the geometrical model of FIG. 5, the arm 26 is jointed to the base 24 by means of a first joint J1 which is a prismatic sliding (P) joint (or rectilinear translation joint). The first joint J1 is connected to the base 24 by means of a base link L0 and provides a translational DOF along an essentially vertical axis. The first joint J1 hence allows vertical positioning of the first essentially vertical link L1 and the subsequent components attached to the latter with respect to the base 24 and the link L0. In other words, joint J1 defines the height of the vertical part 27. A second joint J2, which is a revolute (R) joint, connects the first link L1 to a second essentially horizontal link L2 of the arm 26. The rotation axis of the revolute joint J2 is essentially vertical. The joint J2 allows to set the relative angle between the link L2 and its initial angular position in a horizontal plane. A third prismatic sliding (P) joint J3 connects link L2 to a third essentially horizontal link L3. The joint (P) J3 provides a translational degree of freedom along an essentially horizontal axis and allows to set the reach or extension of the arm 26, more precisely the horizontal part 29, by horizontal displacement of the link L3 with respect to the link L2. The links L2 and L3 together with the (P) joint J3 form an essentially horizontal extensible jib or boom of the robot manipulator 14.

With two (P) joints and one (R) joint arranged as seen in FIG. 5, the arm 26 has one rotational DOF about an essentially vertical axis, and associated thereto two translational DOF along two perpendicular axes. Accordingly, the arm 26 of the robot manipulator 14 has cylindrical configuration, i.e. the kinematic configuration of the manipulator 14 belongs to the class of cylindrical robots of PRP (Prismatic-Revolute-Prismatic) type. More precisely, each joint among the first three J1, J2, J3 respectively corresponds to a cylindrical coordinate (z, θ, r): z being the elevation (or height) coordinate, θ being the rotational (or azimuth) coordinate and r being the radial elongation (or radius) coordinate.

As further seen in FIG. 5, the wrist 28 comprises two revolute joints J4, J5 and the effector unit 30 includes one revolute joint J6. The revolute joints J2, J4, J5, J6 respectively define the orientation of an adapted laparoscopic instrument 18 attached to the effector unit 30. The revolute joint J4 connects the link L3 to a link L4 and allows to rotate link L4 with the subsequent parts, about an essentially vertical axis that is parallel to the rotation axis of joint J2. Hence, the revolute joint J4 allows to set the yaw angle of the effector unit 30, in combination with the actual setting of joint J2. It should be noted that the axis of rotation the revolute joint J4 is coplanar with the plane formed by the axis of rotation of the revolute joint J2 and by the axis of translation of the prismatic joint J3. The revolute joint J5 connects link L4 to the tool flange 32 and allows to rotate the tool flange 32 with the subsequent parts along an essentially horizontal axis perpendicular to the rotation axis of joint J4. Hence, the revolute joint J5 allows to set the pitch angle of the effector unit 30. The effector unit 30 is connected to the tool flange 32 through a link L5. The rotation axis of the revolute joint J6 is substantially perpendicular to the rotation axis of joint J5 and connects link L5 to a link L6. The rotation axis of revolute joint J6 is aligned with link L6 and defines the relative angle of link L6 with respect to its initial angular position. An adapted laparoscopic instrument 18 is connected to link L6. The instrument 18, represented by link L7, is aligned with link L6. The end point of link L7 represents the instrument tip 17.

The cylindrical PRP kinematic configuration of the manipulator 26 has various advantages among which:
 a relatively small contained room occupied by the manipulator structure above the operation table;
 the fact that the manipulator base is at sufficient distance (due to a minimum link offset of the horizontal part 29 of 800 m) from the operation table to facilitate surgeon access to the operation table and patient transfer from/to the operation table;
 easy and fast inter-manipulators collision detection computation.

These and other aspects will become more apparent from the following paragraphs.

Figure 2:
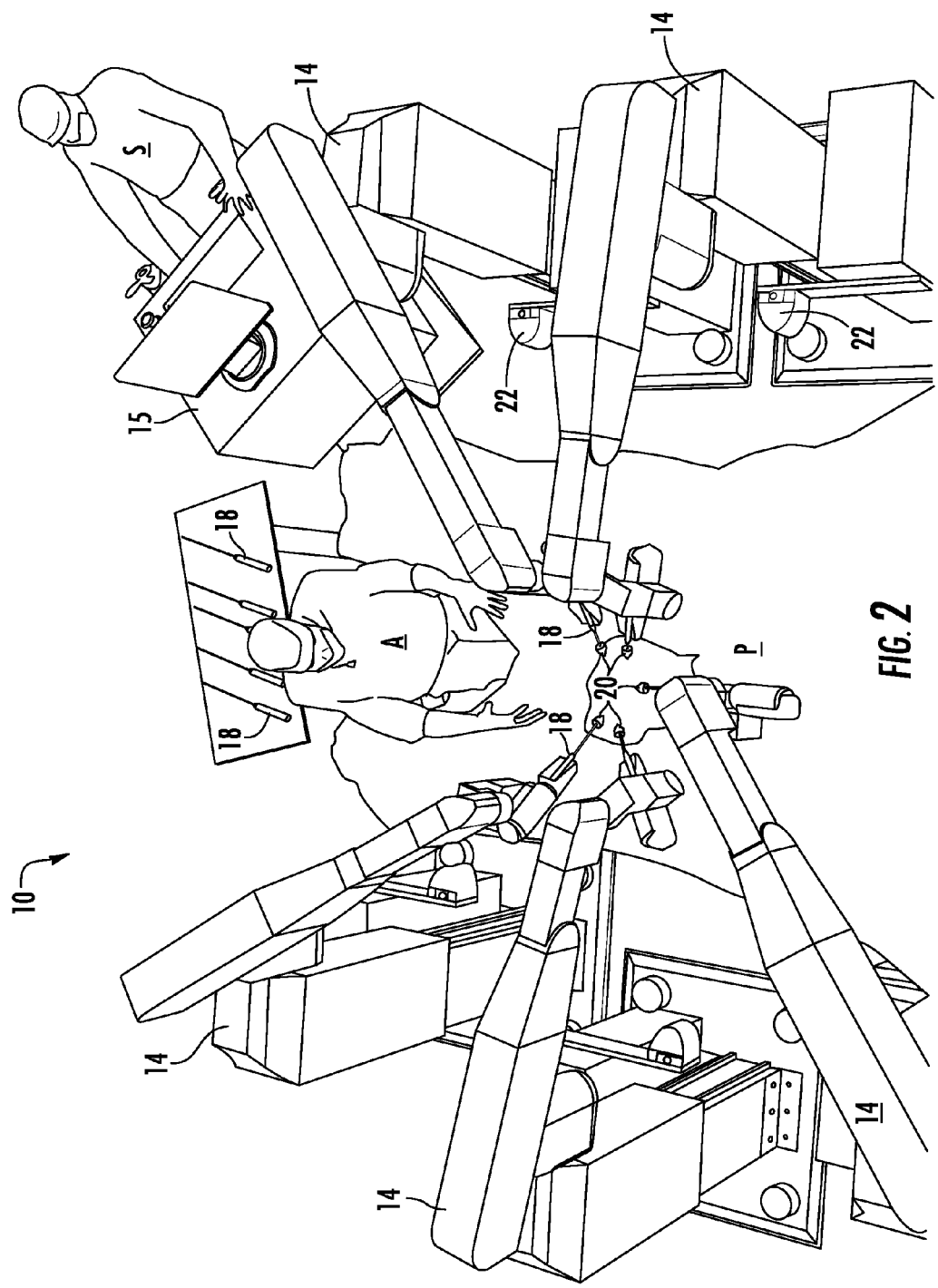
FIG. 2: is a perspective view of a robotic surgical system for generic surgical laparoscopy with five robot manipulators.
Figure 6:
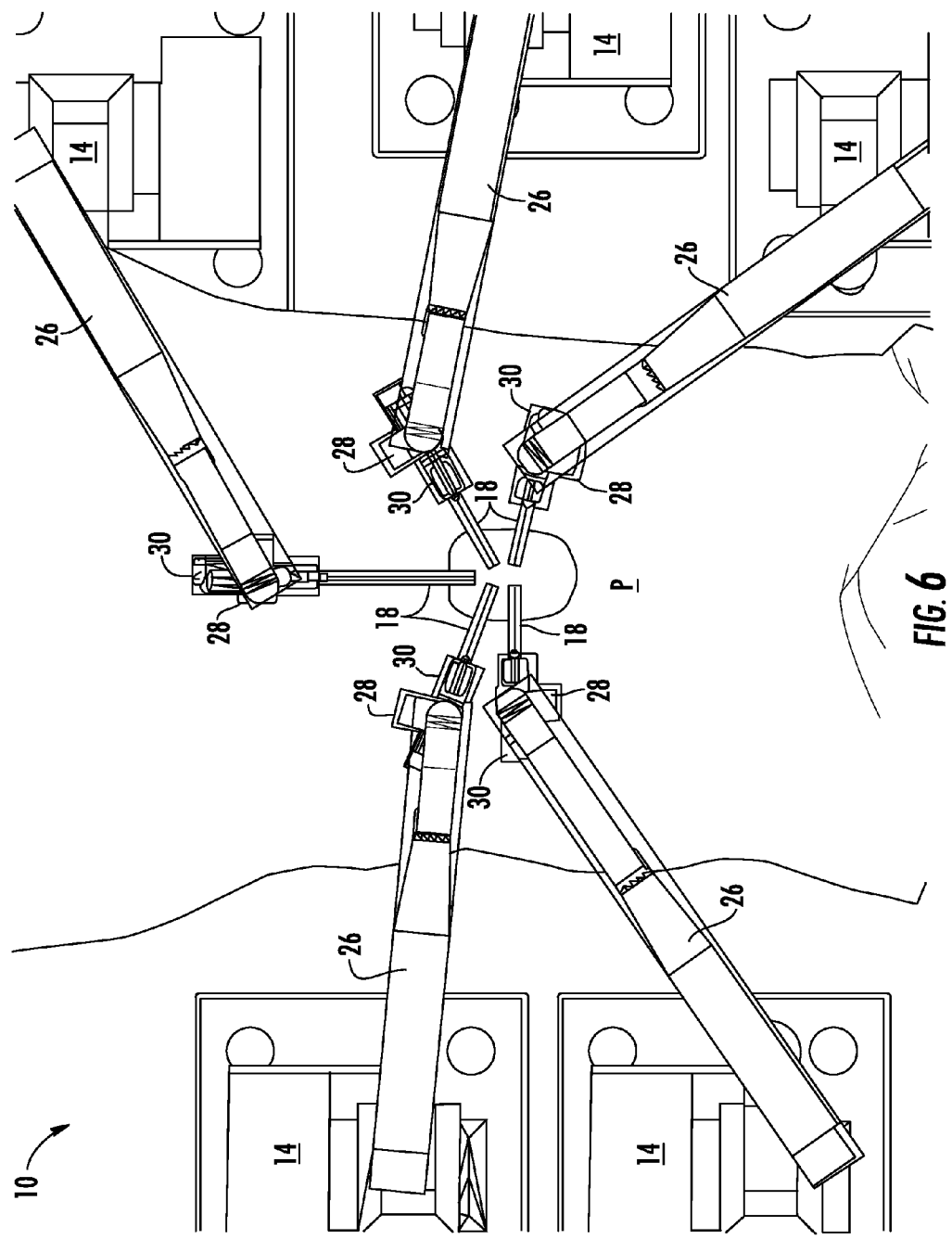
FIG. 6 is a top view of a robotic surgery system with five robot manipulators, illustrating 2D collision detection boxes enveloping manipulator components.

An advantage resulting from the chosen PRP kinematic configuration of the robot manipulator arm 26 is the simplification of collision detection computation between a plurality of manipulators 14 arranged with intersecting workspaces around the operation table 12 (FIGS. 1 and 2). Due to the cylindrical configuration, the robot manipulator 14 can be approximated with simple planar geometrical features in a two-dimensional (2-D) horizontal plane. As best seen in FIG. 6, the mechanical links of the arm 26 can be enveloped by a rectangle of variable length and orientation respectively corresponding to (J3+L2+L3) and to J2; the width of the rectangle envelop is given by the mechanical link geometry plus a margin depending, for instance, on the space required to brake the robot from maximum speed to stop plus a safety threshold. The margin of each side of the rectangle envelops can be dynamically sized according to the direction and speed of motion, e.g. the higher is the velocity in the direction of an envelop side, the higher is the margin for this envelop side. The wrist 28 is approximated by a rectangle enveloping the body of link L4 and part of link L5 and with a variable planar orientation given by the current angular position of joint J4. Similarly, the effector unit 30 can be approximated by a rectangle enveloping its projection on the 2-D horizontal plane where the projection angle corresponds to the current angular position of joint J5. The same principle applies to the stem of the instrument 18 connected to the effector unit 30. Such simple geometrical two-dimensional features permit to establish simple and efficient algorithms for collision detection based on the intersection of their lines. In a first stage, the collision detection method consists of checking a collision in the 2-D horizontal projection. Only if any of these 2-D figures collides with a figure from a different robot manipulator 14, an effective risk of real collision is subsequently verified by including the third dimension. As will be appreciated, 3-D calculations therefore need to be carried out only for the intersecting sides of the concerned parts of the robot manipulators 14. In this simplified 3-D calculation, the concerned parts are enveloped, for example, with a triangular-based model. As a result fast intersection-detection algorithms can be easily implemented, e.g. those proposed in "A Fast Triangle-Triangle Intersection Test" by Moller, Journal of Graphics Tools, 2(2), 1997. In practice, collision detection between stems of instruments 18 is relevant especially to protect the endoscope from powered instruments.

For an accurate result of the collision detection between robot manipulators 14, the position and orientation of all the robot manipulators 14 with respect to a common reference coordinate system is determined through a calibration procedure after the positioning of the manipulators 14 in the operation theatre. From the functional point of view, after the detection of a collision risk, the control system must halt the concerned manipulators 14 and warn the surgeon S through appropriate display information and/or a repulsive force feedback on the master console 15. The surgeon S can then simply achieve recovery by tele-operating one of the manipulators in a safe direction. In a further improvement, several collision-safety levels are implemented using at least two envelopes with different margins for each of the sets of parts, e.g. arm 26, wrist 28, effector unit 30 and/or instrument 18. After detecting a risk of collision with the more protuberant envelope, motion commanded by the surgeon S in the collision direction is sharply scaled down in function of the penetration in the margin area.

Another advantage regarding the configuration of the arm 26 is related to improved controllability of the actuators associated to the joints J1, J2, J3. When compared to other classes of robots (e.g. spherical or articulated robots), and as a result of the arm configuration, control of these actuators is improved because J1, J2, J3 and J4 are not subject to varying gravitational loads, and because J1, J3 and J5 do not have varying inertial loads. This enables simplified optimisation of control loops (e.g. PID with feedforward) and to achieve very low position dynamics tracking errors, e.g. of a few motor encoder counts only. Besides the presented advantages, the mechanical design shall consider a stiff but lightweight structure for links L2 and L3 to limit their deflection and oscillations in case joint J1 and/or joint J2 executes abrupt motion.

Two further advantages resulting from the geometry of the robot manipulator 14 should be noted. Firstly, with the manipulator base 24 located at sufficient distance from the operation table 12 (e.g. at least 600 mm away) and the arm 26 designed such that it can be turned by hand about joint J2 (with brakes released) to a parking position, the surgeon S can readily and rapidly access the operation table 12 for manual tasks such as insufflation, anatomic organ removal, final suturing, etc. Furthermore, transfer of the patient P on to or away from the operation table 12 is rapidly possible. Secondly, compared to a SCARA geometry, used e.g. in the manipulator arm known by the commercial name ZEUS, having an elbow rotation joint connecting two co-planar links of similar length to reach a certain horizontal location, the cylindrical configuration of manipulator 14 has a single radial elongation joint J3 that considerably reduces the space taken to position the wrist 28 above the body of patient P. As shown in FIG. 2, this feature enables five manipulators 14 and more to be positioned at the operation table 12 providing that the dimensions of the wrist and of the effector unit be sufficiently small, i.e. occupy a sufficiently contained space in the available workspace above the patient body.

In the following paragraphs a more detailed description of the construction of the robot manipulator 14 will be given by reference to FIGS. 7 to 15.

Figure 7:
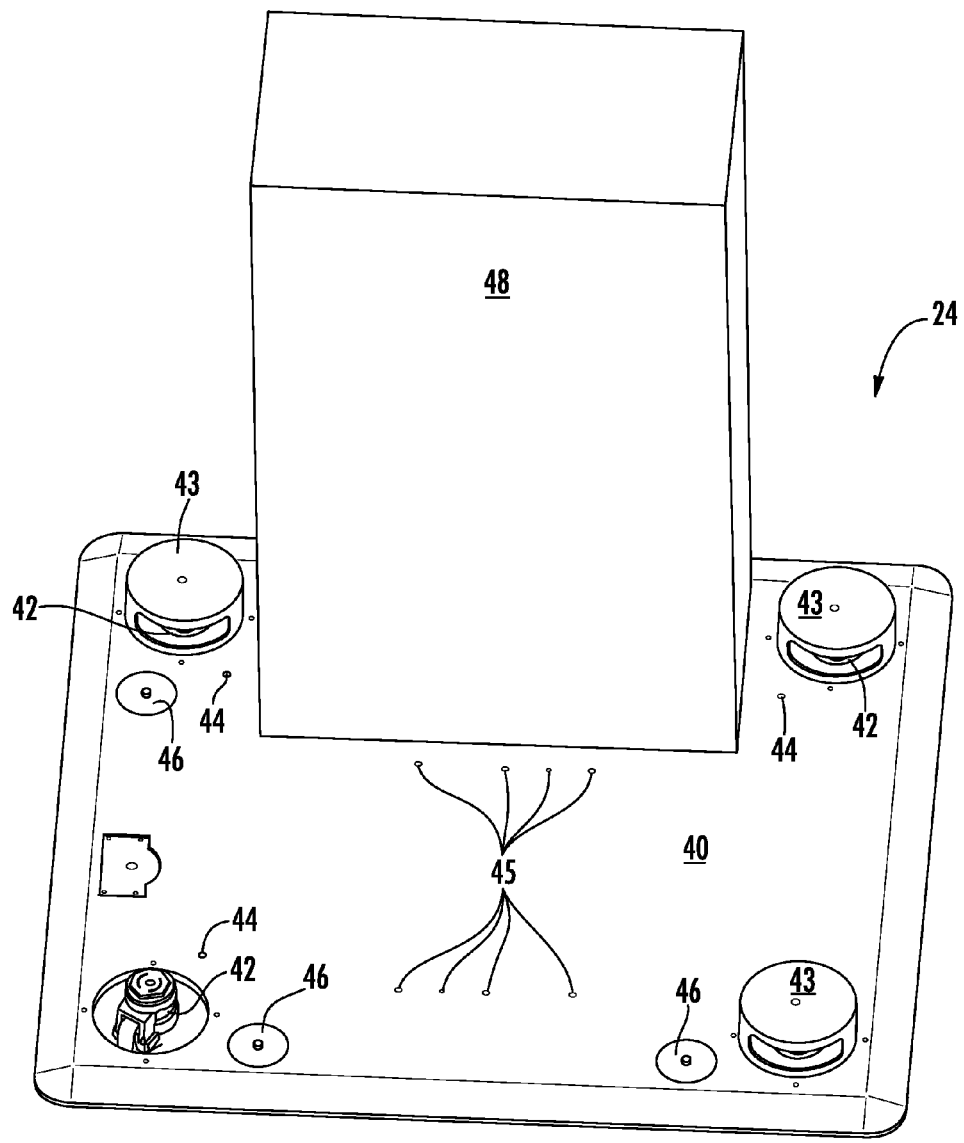
FIG. 7: is a perspective view of the base of the robot manipulator of FIG. 3.
Figure 8:
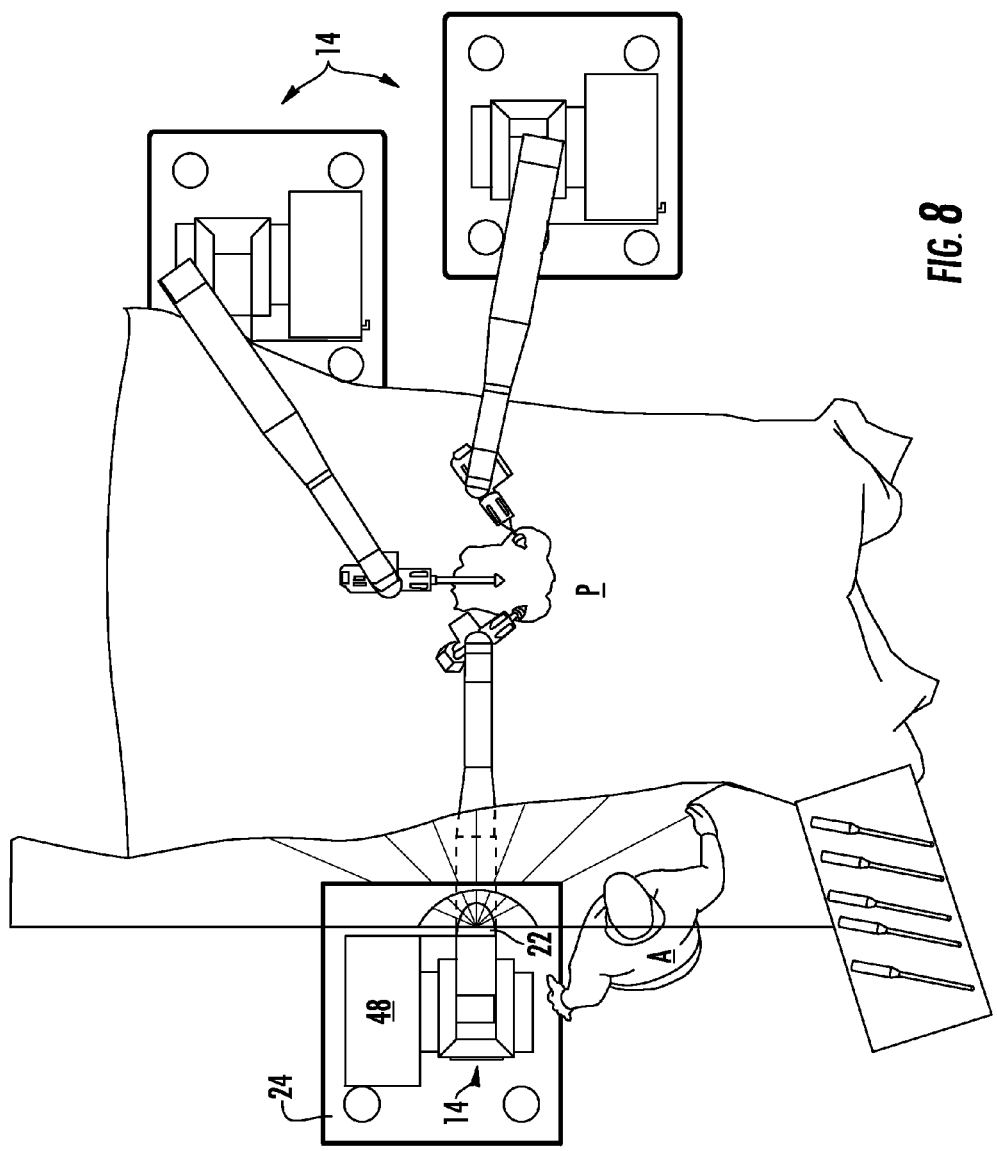
FIG. 8 is a top view of a robotic surgical system showing a 2D laser based detection to detect proximity of a surgeon assistant with respect to a robot manipulator.

FIG. 7 shows several features of the base 24. The base 24 includes a main base plate 40 and is arranged as moveable structure by means of four wheels 42 installed in openings at the corners of the main plate 40. Each wheel 42 is enclosed in a cover 43 with an opening for access to a handle for extracting or retracting the wheels 42. When the wheels 42 are retracted, the base 24 rests stable on the floor of the operation theatre by means of cushion supports (not shown) of the wheels 42. After extracting the wheels 42, the base 24 including the robot manipulator 14 can be moved by hand. In a different design, the base 24 can be mounted on a moveable or fixed linear rail axis or on a cart designed to support several bases 24 and associated manipulators 14. The main base plate 40 is designed such that it can be fixed to the floor if necessary, e.g. by screwing using holes 44, in order to give additional stability to the robot manipulator 14. The robot manipulator 14 is attached to the base 24 through bolts in threaded holes 45. In the base plate 40, several high precision bores 46 are machined. The bores 46 serve to support optical calibration reflectors which are used to determine the position and orientation of the base 24 by means of an optical measurement system, as described in "Robot calibration" by R. Bernhardt and S. Albright, ed. Chapman & Hall, 1993. It may be noted that the robot manipulator 14 is calibrated during the factory set-up procedures in order to accurately determine its geometrical model. Furthermore the base comprises an enclosure 48 for power supply and servo-drives of brushless motors, signal conditioning devices, means for local processing of arm-mounted sensors, and communication channels to a remote system control unit. As shown in FIG. 1 and best seen in FIG. 8, a 2D laser range scanner 22 is installed on the base 24, more precisely on the enclosure 48, to enable detection of intrusion, e.g. by assistant A, inside a safety perimeter around the links L2 and L3.

It should be noted that generally two different types of robot manipulators 14 are used in the robotic surgical system 10. Although the two types of robot manipulators 14 essentially have the same geometry and kinematic PRP configuration of the arm 26, the first type is preferably specifically arranged to handle an endoscope used for visualization whereas the second type is arranged to handle any of various kinds of adapted laparoscopic instruments 18 used for operation per se. For laparoscopy, normally one robot manipulator 14 of the first type is used whereas several robot manipulators 14 of the second type are used. In the robotic surgical system 10, the major differences between these two types of robot manipulators 14 are:

- travel of joint J3 is longer for an endoscope manipulator (about 750 mm) because it requires 360° rotation around its access port (usually for exploration purposes).
- travel of joint J4 is infinite for an endoscope manipulator because it requires 360° of rotation around the access port. This is enabled by use of a signal collector on the J4 axis.
- joint J6 is not needed for the endoscope manipulator, i.e. the endoscope can be attached directly to the joint J5.
- the effector unit 30 of an endoscope manipulator normally consists of the endoscope and of a force/torque sensor to detect extra-forces
- speed/acceleration requirements for all joints are lower by min. 60% for an endoscope manipulator because it requires positioning capability for the endoscope only.

Taking into account these differences, the present description is focused on the second type of robot manipulator 14, since the latter has the more stringent design requirements.

Figure 9:
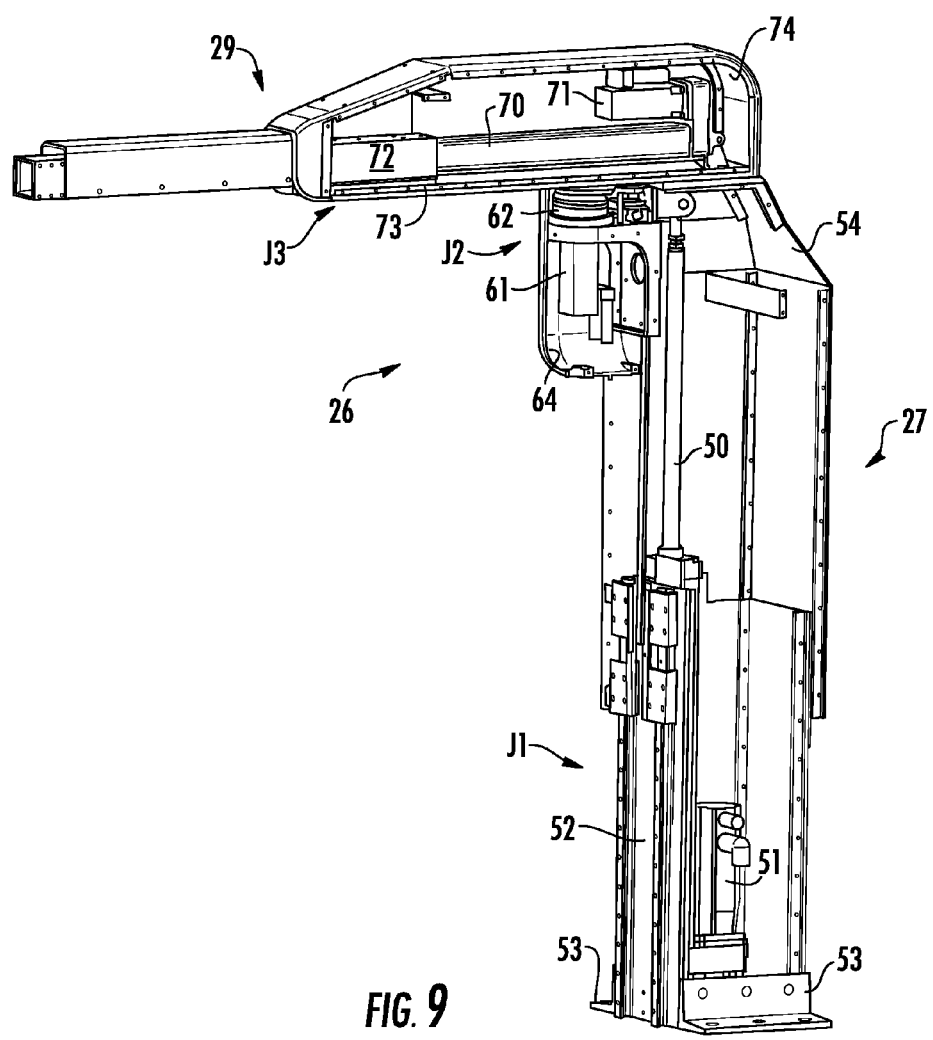
FIG. 9: is a perspective view of the internal components of joints J1, J2 and J3 of the robot manipulator of FIG. 3.

Referring to FIG. 9, details regarding the configuration of joints J1 to J3 of the manipulator arm 26, including their respective actuators, are given below.

As associated linear actuator, the (P) joint J1 for arm elevation comprises a ball screw linear axis 50 (for example a suitable model of the ET series produced by Parker Hannifin, Electromechanical Division, Offenburg, Germany & Poole, UK). The ball screw linear axis 50 is driven by a brushless servo-motor 51 equipped with an incremental motor position encoder and a brake. The linear axis 50 is additionally provided with an additional absolute linear position sensor (not shown) at the output stage, with limit switches and with a mechanical end-of-travel bumper (not shown). A vertical linear guide 52 is operatively associated to the linear axis 50 in order to ensure axis linearity and torsion stiffness. The linear axis 50 is attached to brackets 53 for mounting the arm 26 to the base 24. Signal and power wires are guided in a vertical cable channel (not shown) inside the cover of the joint J1. An external cover 54 encloses the components of the prismatic (P) joint J1 as best seen in FIG. 3. Regarding the actuator assembly of joint J1 it may be noted that the motor/load reduction ratio is set such as to prevent undesired falling of the horizontal part 29 also when the motor brake is disengaged or when the servo-motor 51 is not powered. In addition, an emergency stop button (not shown) is placed on the external cover 54, which serves to stop motion of all robot joints in case of an emergency. As seen in FIG. 9, the aforementioned components of the manipulator arm 26 constitute its essentially vertical part 27.

Figure 10:
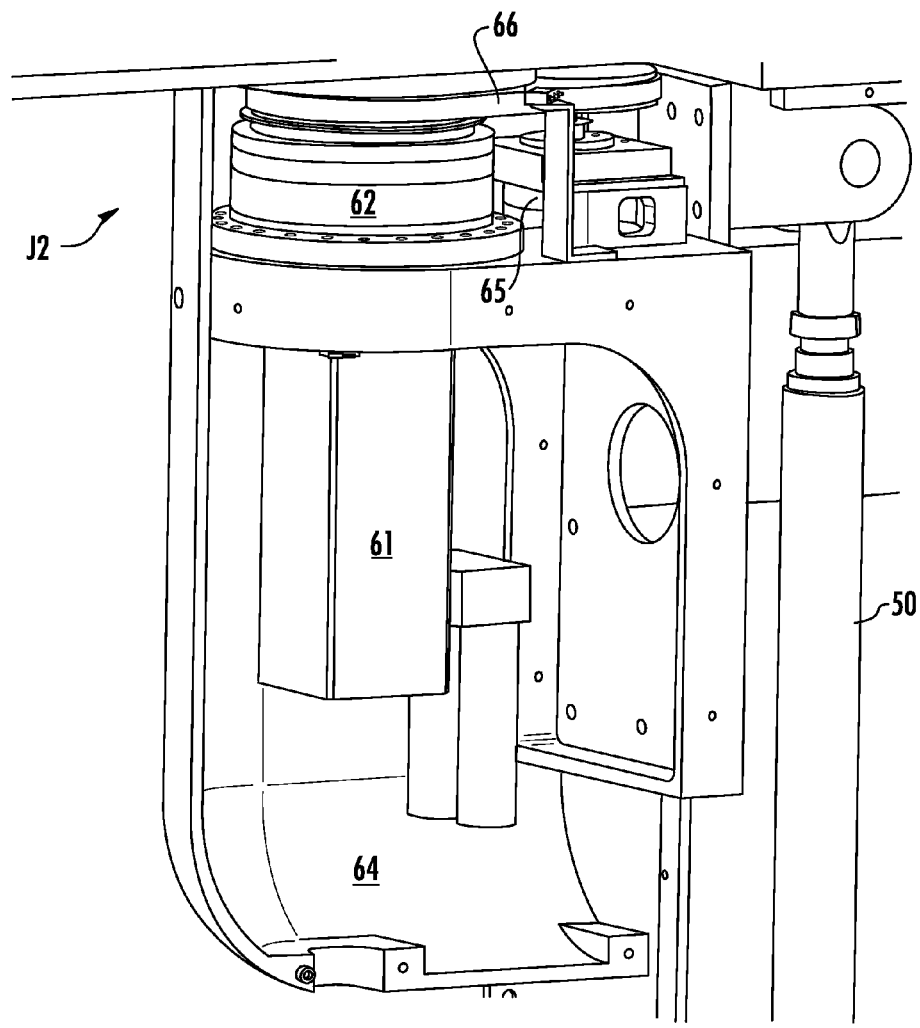
FIG. 10: is a perspective of the internal components of joint J2 of the robot manipulator of FIG. 3.

FIG. 9 also shows the (R) joint J2 forming the shoulder joint of arm 26. As best seen in FIG. 10, joint J2 comprises an assembly of a brushless servo-motor 61 in-line with a gear 62 of the Harmonic Drive® type to drive the load. The brushless motor 61 is equipped with a position encoder and a fail-safe brake. In addition, the actuator assembly comprises a further absolute rotary position sensor 65, which is driven by a belt 66 connected to the output stage of the gear 62, and mechanical end-of-travel bumper and limit switches (not shown). A key switch (not shown) is provided on cover 64, which allows to release brakes of the joints J2, J3, J4, J5 and J6 when their respective motors are not powered. This allows to move the arm 26 and the effector unit 30 by hand into a parking position. Signals and power cables from downstream joints J3 to J6 and from the effector unit 30 are routed from J3 to J1 through a flexible cable duct (not shown) which passes inside the cover 64. Alternatively, such cables could be guided for instance through the hollow-shaft of an adapted gear and motor assembly.

FIG. 9 also shows the design of the horizontal part 29 of the arm 26 including (P) joint J3 for setting the radial extension, i.e. reach of the horizontal part 29. Joint J3 comprises a linear cylinder axis 70, e.g. a ball screw linear axis, as associated linear actuator. For example, an ET model actuator produced by the aforementioned company, driven by a brushless servo-motor 71 equipped with a motor position encoder and a fail-safe brake is used. The rod of the linear cylinder 70 axis moves a beam 72 which is configured as rectangular tube and mounted on trolleys of a linear guide 73. This construction allows reducing linear deflection. The linear cylinder axis 70 is additionally provided with an additional absolute linear position sensor at the output stage, with limit switches and with end-of-run mechanical bumpers (not shown). Signal and power lines are guided in a horizontally placed cable chain. A covering 74 is fixed to the parts forming the second link L2 and encloses the components of the (P) joint J3, in particular the linear actuator 70 and the linear guide 73. As seen in FIG. 9, the beam 72, which forms part of link L3, is configured for telescoping into respectively out of the covering 74. The arm 26 is thereby provided with a horizontal part 29 narrowing into an extremity which requires only a limited amount of space above patient P. Furthermore, lamps are preferably provided on the rear-top of the covering 74 to visually indicate the power and activation status.

By reference to FIGS. 11-13, the construction of wrist 28 and more particularly the joints J4 and J5 will be detailed below.

Figure 11:
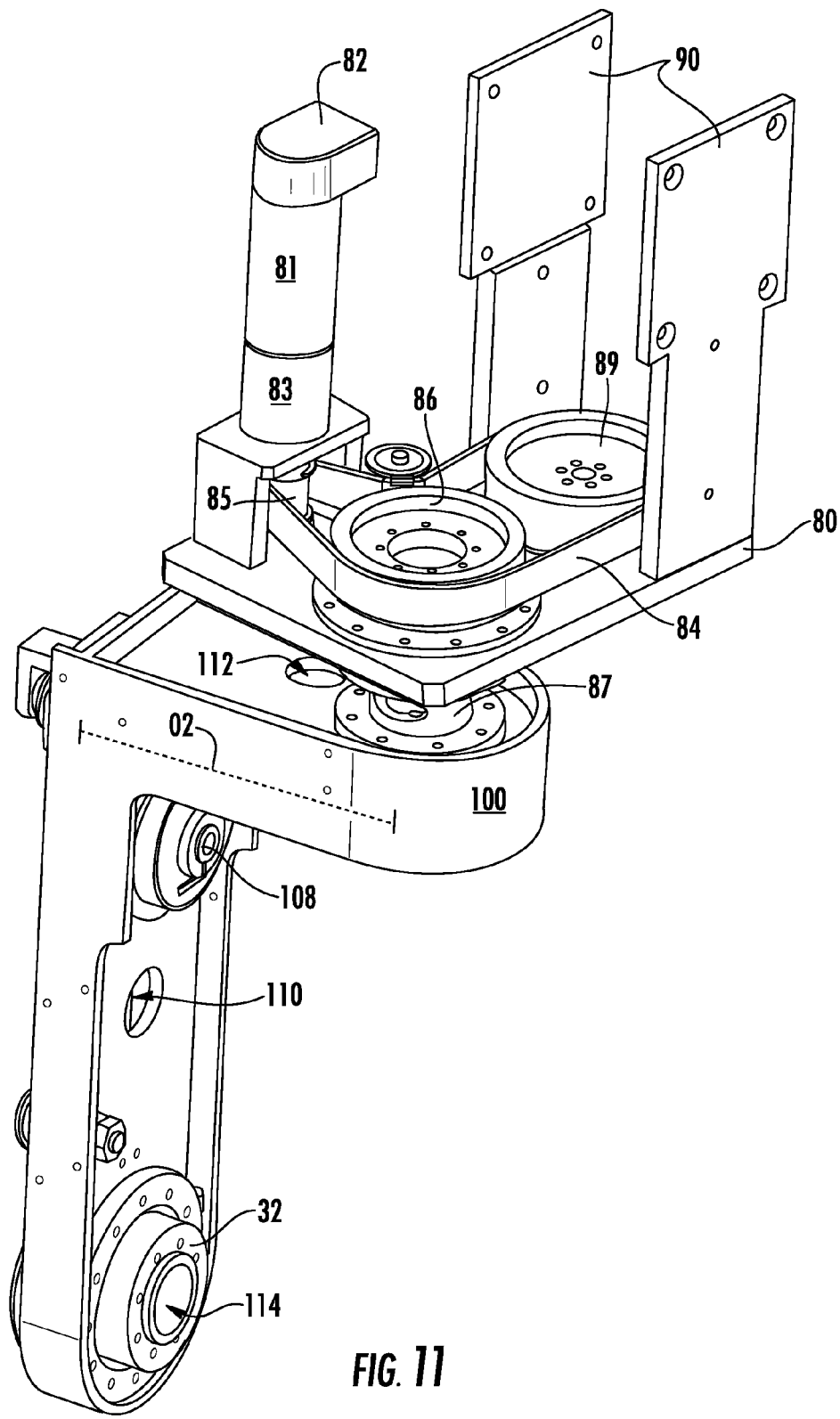
FIG. 11: is a first perspective view of internal components of the manipulator wrist including joints J4 and J5.
Figure 12:
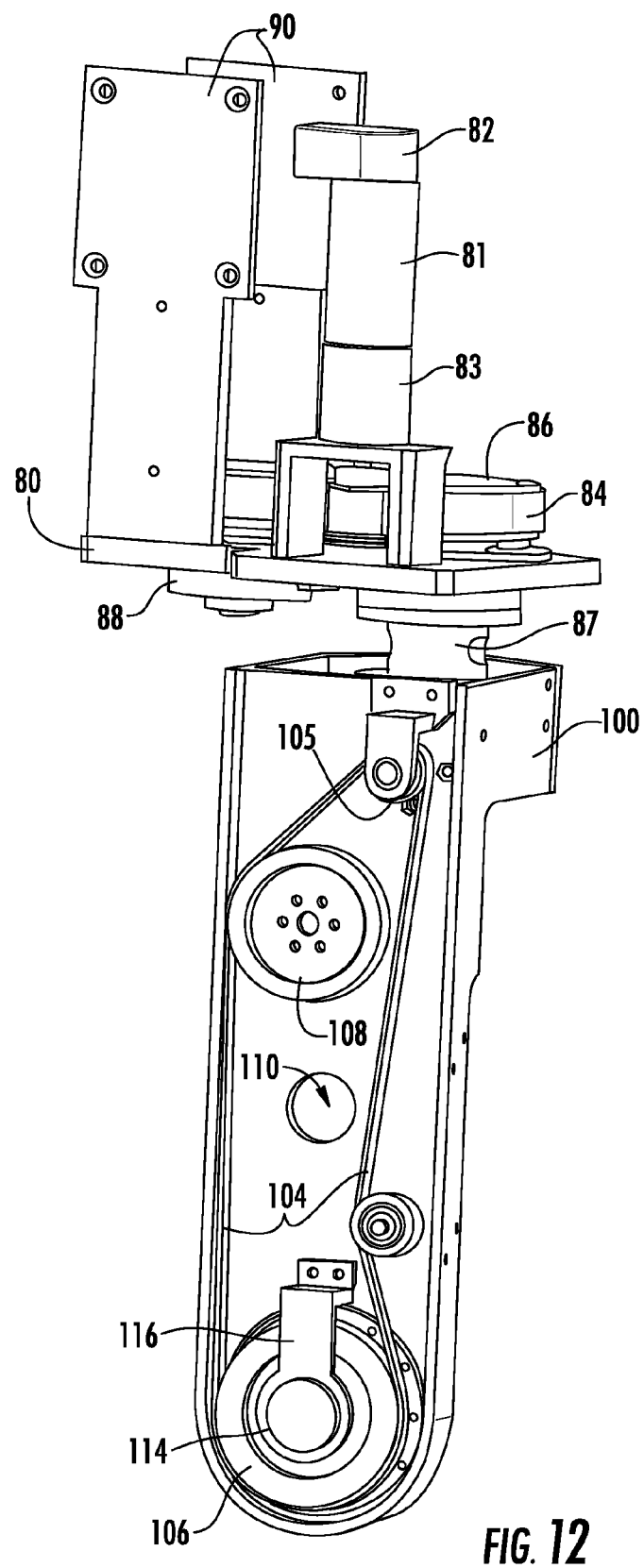
FIG. 12: is a second perspective view of internal components of the manipulator wrist including joints J4 and J5.
Figure 13:
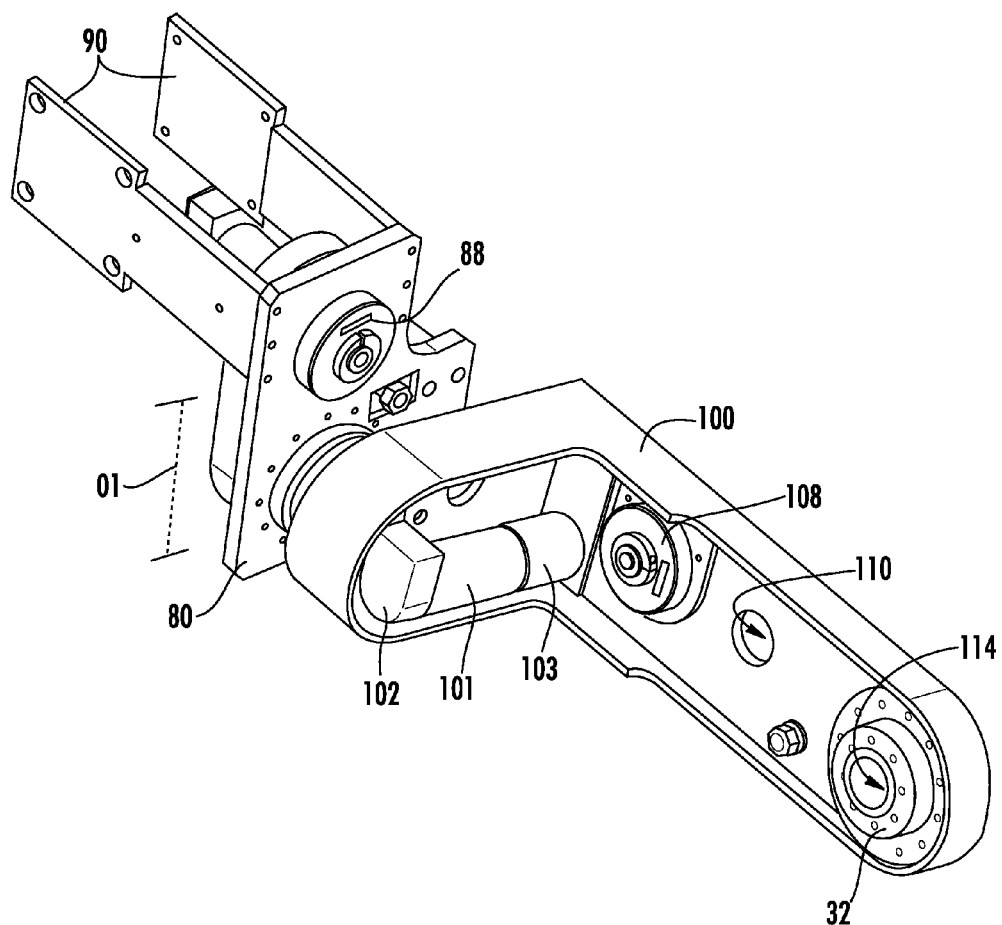
FIG. 13: is a third perspective view of internal components of the manipulator wrist including joints J4 and J5
Figure 14:
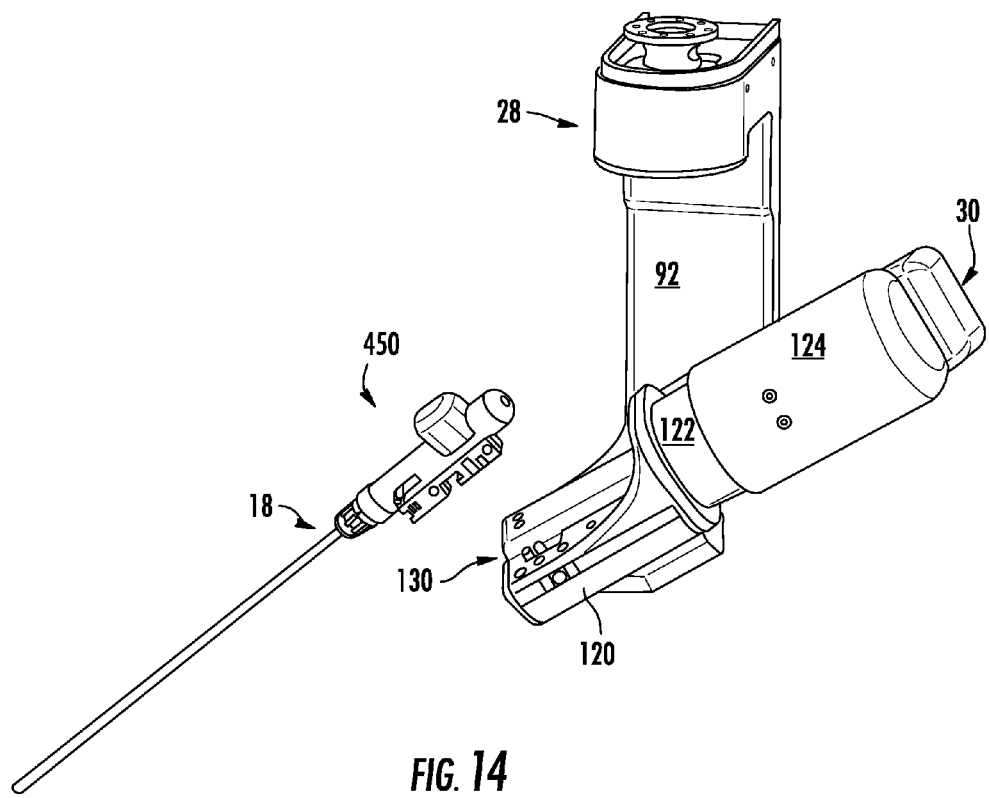
FIG. 14: is a perspective view showing an effector unit of the robot manipulator of FIG. 3 and an adapted instrument to be connected to the effector unit.

The mechanical and actuation design of (R) joint J4 shown in FIGS. 11-13 comprises a support plate 80 to which a brushless servo-motor 81 is mounted vertically. The servo-motor 81 is provided with a position encoder 82 and a hall sensor on the motor shaft. As servo-motor 81, a suitable model of the EC motor series from MAXON MOTOR A. G., Sachseln, Switzerland is used for example. The (R) joint J4 further comprises a transmission mechanism through a gear 83 coupled to the servo-motor 81 and through a transmission belt 84 and pulley 85 system to drive a load axis pulley 86 which is coupled to a connection flange 87. An additional absolute single-turn sensor 88 is connected to a pulley 89, which is also driven by the transmission belt 84, and attached to the bottom side of the support plate 80. In order to easily route cables from joint J5 to joint J4, the assembly comprising the load axis pulley 86 and the connection flange 87, has a hollow shaft and a lateral window on the connection flange 87. The support plate 80 is stiffly attached to the beam 72 by means of two mounting plates 90. As seen in FIG. 14, a cover 92 serves to protect to parts of joint J4. Inside the cover the cables from the effector unit 30, from joints J5 and J4 are provided with connectors to make the wrist 28 detachable for maintenance purpose. An emergency stop button is provided on the cover 92 of joint J4. A fail-safe brake is preferably mounted on the shaft of the servo-motor 81. In order to reduce the lateral offset O1, which could constitute a limiting factor in a multi-robot configuration, the motor can also be aligned with the axes of the load axis pulley 86 and the sensor 88. In this case, the support plate 80 preferably has a rounded border around the load axis pulley 86.

The mechanical and actuation design of (R) joint J5 is also shown in more detail in FIGS. 11-13. An essentially L-shaped support member 100 links the joint J5 to the joint J4, with a horizontal portion connected to joint J4 and a vertical portion as fixed frame for joint J5. It comprises a brushless servo-motor 101, for example a suitable EC model of MAXON MOTOR A.G., with a position encoder 102 and a hall sensor on the motor shaft. As seen in FIG. 13, the servo-motor 101 is mounted transversely on the support member 100. As seen in FIGS. 12 and 13, the (R) joint J5 further comprises a transmission mechanism through a gear 103 coupled to the motor 101 and a transmission belt 104 and pulley 105 system to drive a load axis pulley 106. An additional absolute single-turn sensor 108 is connected to a pulley 109 which is also driven by the transmission belt 104, and attached to the inner side of the support member 100. In order to easily route cables from the effector unit 30 to joint J4, a number of features are included. These are two holes 110 and 112 provided in the support member 100, a hollow central passage 114 in the pulley 106 and the tool flange 32, and a cable routing support 116 for the pulley 106. The L-shaped support member 100 has lateral reinforcements to provide a rigid structure for supporting the effector unit 30 through the tool flange 32. If required, the (R) joint J5 preferably includes limit switches and a fail-safe brake (not shown). When provided, the latter are preferably mounted on a pulley driven by transmission belt 104 in order to reduce lateral offset O2, which may constitute a limiting factor in a multi-robot configuration.

Figure 15:
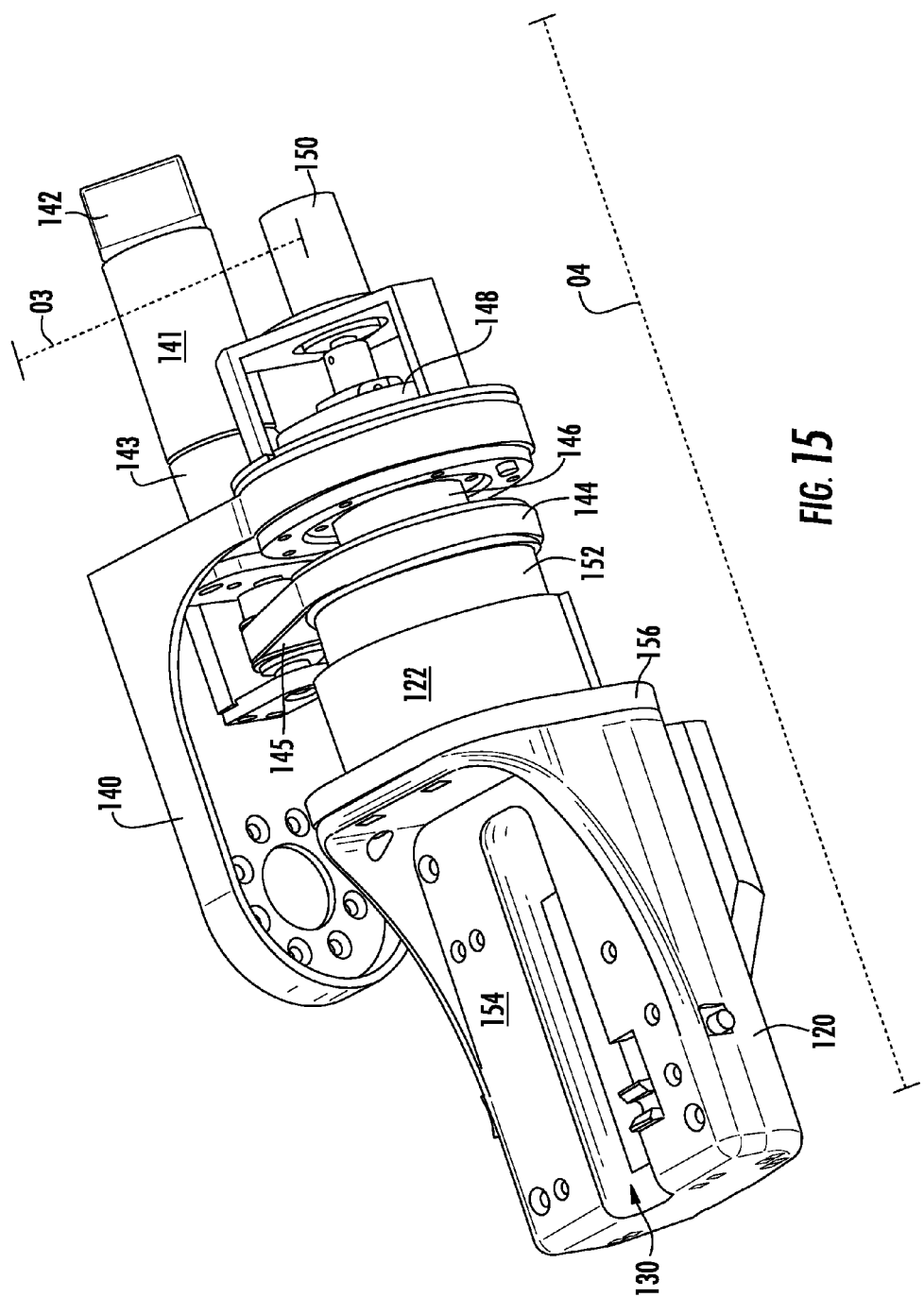
FIG. 15: is a perspective view of main internal components of the effector unit of FIG. 14.

FIGS. 14 and 15 show the effector unit 30, designed to be connected to the tool flange 32 of joint J5, with its three main parts: a laparoscopic instrument actuator 120, a sensor assembly 122 including a 6 DOF force/torque sensor and a 6 DOF linear/angular accelerometer, and a cover 124 for joint J6. Joint J6 is connected to the sensor assembly 122. The laparoscopic instrument actuator 120 is provided with a seat 130 for mounting an adapted laparoscopic instrument 18 to the robot manipulator 14.

For alleviation, the laparoscopic instrument actuator 120 and the sensor assembly 122 including force, torque and acceleration measurement sensors shall be referred to by the acronym LIA and FTAS respectively. The components of the effector unit 30 are aligned in such a way that joint J6 rotates the adapted laparoscopic instrument 18 about the latter's longitudinal axis of symmetry, and such that this axis coincides with the normal Z axis of the FTAS 122. The position of the effector unit 30 with respect to the rotation axis of (R) joint J5 is selected at the equilibrium point of the effector unit 30 such as to avoid tilting when joint J5 is stopped and not powered. Hence, a main support frame 140 of the effector unit 30, which connects to the wrist 28, is configured such that the assembled effector unit 30 is balanced on the rotation axis of (R) joint J5. The motor/load reduction ratio for joint J5 also contributes to the tilting resistance.

FIG. 15 shows the construction of the joint J6. To the main support frame 140 (to be connected to the tool flange 32) is mounted a brushless motor 141 with an incremental encoder 142 and a gear assembly 143. A motor pulley 145 connected to the motor 141 is coupled to a load pulley 146 by means of a belt 144. The load pulley 146 provides the rotational DOF of joint J6. An additional absolute position sensor 148 is mounted on the axis of the load pulley 146 coinciding with the axis of (R) joint J6. The position encoder 148 has a hollow shaft for passing signal and power lines of the LIA 120 and FTAS 122 to a rotating collector 150 of the "slip-ring" or sliding contact type. The slip-ring 150 enables infinite axis rotation for joint J6. The load pulley 146 is connected to the FTAS 122 through a connection flange 152. Cables for power and signal lines for the LIA 120 and FTAS 122 are guided inside the cover 124 through a hollow passage in the connection flange 152. As will be appreciated, the robot manipulator 14 as a whole is provided with internal channels to ensure protected guiding of all signal and power lines e.g. of joints J1-J6 and effector unit 30 components such as LIA 120 and FTAS 122. In a further improvement (not shown) the configuration of joint J6 implements the following two modifications: Firstly, reduction of the offset O3 by locating the motor-gear-pulley assembly 141, 143, 144, 145 at −90 degrees with respect to the orientation shown in FIG. 15. Secondly, the offset O4 is reduced by configuring the motor-gear assembly 141, 143 to be located closer to the LIA 120.

As will be appreciated, the rotation axes of joints J4, J5 and J6 intersect at the same point in space in the presented embodiment. Thereby a potential offset caused by link L5 is eliminated.

Figure 23:
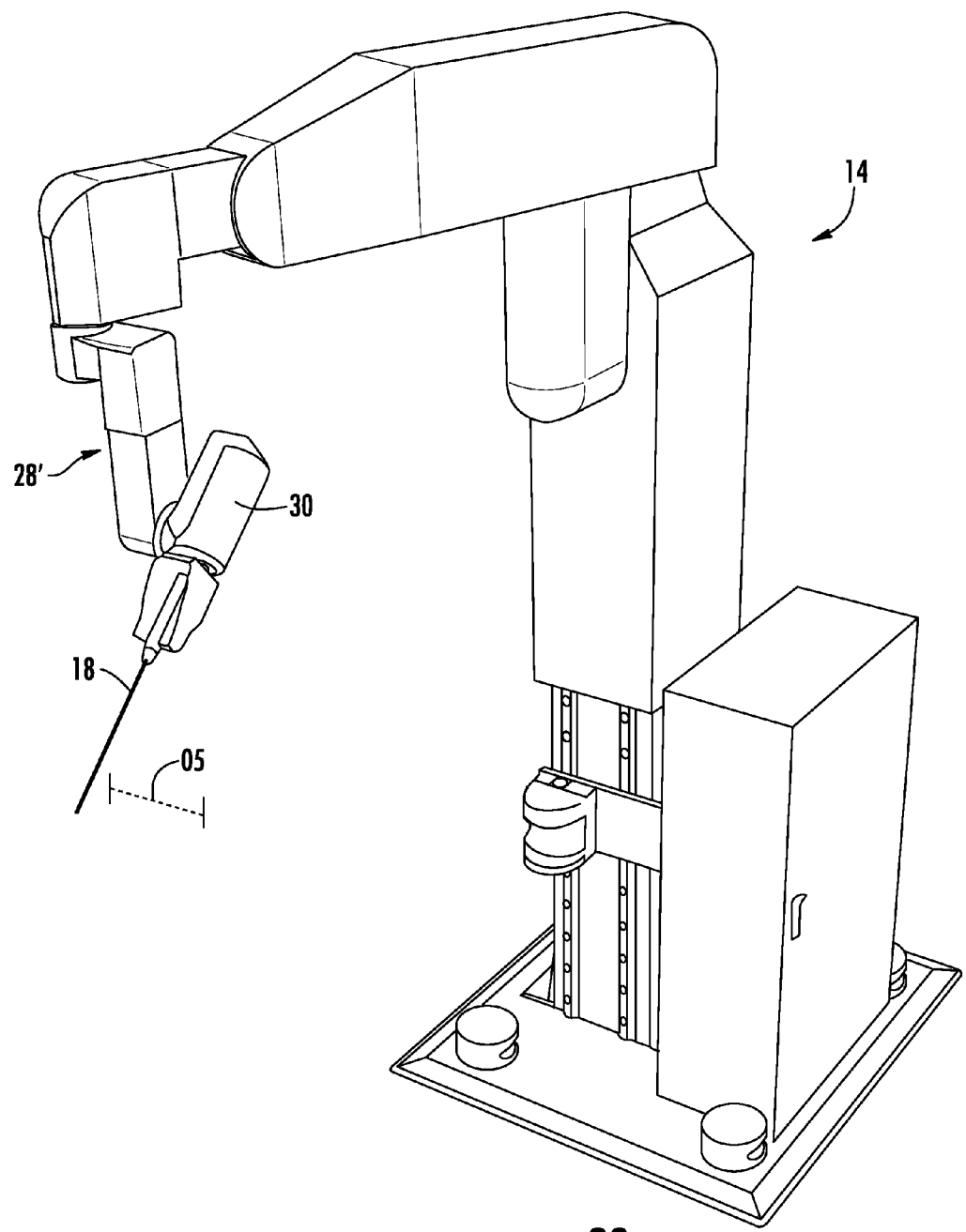
FIG. 23: is a perspective view of a robot manipulator according to FIG. 3 having a modified manipulator wrist.
Figure 24:
FIG. 24: is a perspective view of a robotic surgical system for generic surgical laparoscopy with four robot manipulators according to FIG. 23 and one robot manipulator according to FIG. 3.

As shown in FIG. 23 and FIG. 24, an alternative design could however present an offset O5 due to link L5 e.g. in order to improve manoeuvrability in case two adapted laparoscopic instruments 18 are to be inserted in nearly located trocars (access ports 20). For instance, the specific design shown in FIGS. 23 and 24 provides a modified manipulator wrist 28' having a negative offset O5 due to link L5. This negative offset O5 allows to place the effector unit 30 of a first robot manipulator 14 above the effector unit 30 of a second robot manipulator 14 without collision between the wrists 28'. This modified configuration requires however an increased reach for joint J3 and higher speed and acceleration capabilities for joints J2, J3 and J4. As will be appreciated from FIG. 24, the configuration of the wrist 28' is advantageous for operating at multiple closely located access ports 20 (trocars 200). It will be understood that a preferred value of the offset O5 between the axis of rotation of J6 and J4 as shown in FIG. 23 is approximately the diameter of the LIA 120 at its largest cross-section.

Some further aspects and advantages regarding the design of the robot manipulator 14 and its components will be detailed below.

As regards the described configuration of transmissions and motors used for the wrist 28 and the effector unit 30, other configurations are also possible using, for instance, cables and pulleys as transmission means or compact gear-motor-brake assemblies with torque motors. Cables and pulleys as transmissions are however more difficult in implementation and to maintenance, whilst assemblies based on torque motors are generally less compact. For the safety of the described system, servo-drives were selected which have a 'dynamic brake' function to allow stopping the motors 51, 61, 71, 81, 101, 141 in case of an emergency stop. The external cover of the robot manipulator 14 is made of a suitable cleanable plastic material and possibly in part of aluminium but all external conductive parts are connected to electrical ground. All internal components are shielded against EMI regarding reception and emission. Regarding sterilization in the operation theatre, a sterile plastic bag is normally used to cover the robot manipulator 14 completely, i.e. from the effector unit 30 to the base 24.

Regarding actuation, the design of the robot manipulator 14 as described above presents two further advantages:

Firstly, the joints of the robot manipulator 14 can be actuated manually, except for joint J1 because it presents high static friction and reversed inertia. In other words, when all brakes are disengaged, the effector unit 30 mounted to the wrist 28 at flange 32 can be moved by hand through manual actuation of joints J2, J3, J4, J5 and J6 requiring a pushing force less than 5 kg only (in horizontal direction). Secondly, system safety is increased by sensorial redundancy. As described above, each one of the joints J1 to J6 has both a position encoder on the motor shaft and an additional position sensor (e.g. 65, 88, 108, 148) measuring the effective motion output of the respective joint. In practice, this sensorial redundancy is used to detect failures (e.g. of a motor wire, of a belt or of a servo-drive).

Furthermore, the design avoids end-of-run conditions at each of the joints J1 to J6. End-of-run occurs when a joint runs out of its motion limit and is a critical condition particularly in tele-operated robotic surgery, because it is difficult and cumbersome for the surgeon S to achieve recovery with an instrument 18 inserted in the body of patient P. In order to avoid end-of-run conditions, the prismatic joints J1, J3 of the arm 26 are designed with sufficient travel and the roll joint J6 of the effector unit 30 is designed for unlimited rotation. As a result, avoidance of end-of-run conditions requires only certain pre-determined initial configuration and set-up conditions to be respected.

Figure 16:
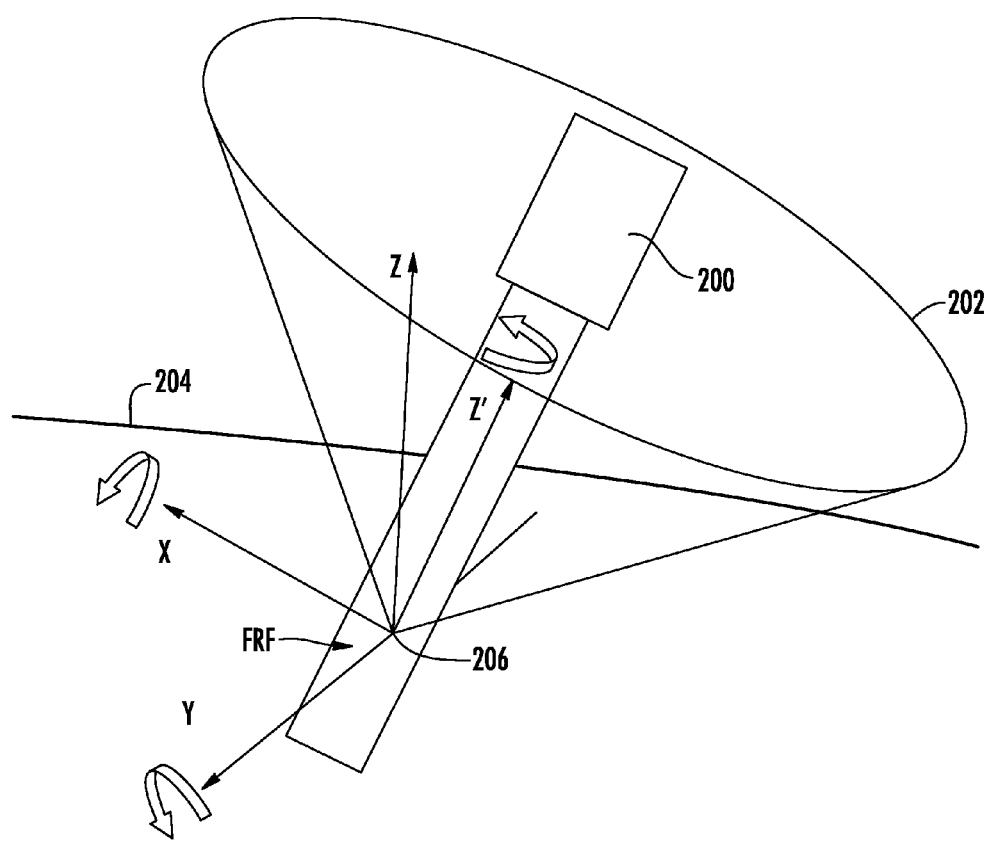
FIG. 16: is a perspective view of a fulcrum reference frame.

FIG. 16 schematically shows a trocar 200 and its workspace 202 external to the body of the patient P. A fulcrum reference frame FRF is also shown in FIG. 16, by means of a Cartesian coordinate system (x,y,z) with the z axis oriented upwards approximately parallel to the direction of gravity. The trocar 200 is normally introduced through a small incision in the abdomen of patient P, indicated at 204, into the peritoneal cavity. The trocar 200 together with the incision forms one access port 20 as shown in FIGS. 1 and 2. In order to reach the organ or region in which an operation is to be carried out, the longitudinal axis of the trocar 200 indicated by z' is pivoted in the workspace 202 about the origin of the FRF, named pivot point 206. In other words, this origin defines a fulcrum for the trocar 200. The fulcrum is preferably determined in between the abdominal wall and the skin of the patient P, at the minor tilting resistance location, in order to reduce the risk of pulling out the trocar 200.

The following maximum force and torque ranges were experimentally registered at a 6 DOF force/torque sensor placed at the handle of a modified laparoscopic instrument (see "*Surgeon-Tool Force/Torque Signatures—Evaluation of Surgical Skills in Minimallyl Invasive Surgery*." by J. Rosen et al—Proceedings of Medicine Meets Virtual Reality, MMVR-7, IOS Press, San Francisco, Calif., January 1999):

Forces: Fx, Fy=±10 N; Fz=±30N;
Moments: Mx, My=±1 Nm; Mz=±0.1 Nm.

Herein Fi represents the force along the corresponding axis i=x, y or z and Mi represents the moment about the corresponding axis i=x, y or z of the FRF in FIG. 16. The operational ranges of the force-torque sensor in the FTAS 122 shall take into account these values plus the weight of the LIA 120, the motion dynamics loads and pivoting and penetration resistance exerted onto the trocar 200. In practice, the force-torque sensor in the FTAS 122 is used for force/torque reflection, i.e. force/torque feedback to a haptic interface operated by the surgeon S, for manually driving the effector unit 30 using the FTAS 122 as a joystick, and for monitoring force/torques interacting with an instrument 18 connected to the effector unit 30, e.g. the forces/torques at the tip of the instrument 18 or at the pivot point 206 in FIG. 4. The linear and radial accelerometer in the FTAS 122 are used for compensating gravity and acceleration influence on the force-torque sensor information. The measurement axes of the accelerometer and force-torque sensor in the FTAS 122 are geometrically coincident.

During operation, a laparoscopic instrument 18 is inserted through the trocar 200. For most surgical procedures, the surgeon S operates the instrument 18 within the following maximum ranges of angular workspace and speed about the FRF of FIG. 16:

TABLE 1

| Fulcrum axis | Max Travel | Max Speed |
|---|---|---|
| Yaw Pivot | +/−70° | 100°/s |
| Pitch Pivot | [+10° −80°] | 60°/s |
| Penetration | [0 200 mm] | 200 mm/s |
| Roll | [−360° +360°] | 300°/s |

In the design and configuration of some prior art robot manipulators, the pivot point of the trocar 200 remains fixed after the wrist installation thanks to the mechanical arrangement of the wrist structure that pivots around a fixed point (see for example: "*Remote center of motion robot*" by Taylor et al.—U.S. Pat. No. 5,667,323—May 1995). Other prior art designs implement a mechanical compliance along pivot axes in order to limit forces applied to the trocar (see for example: "*Medical robotic system*" by Wang et al.—U.S. Pat. No. 6,102,850, August 2000). As opposed thereto, the robot manipulator 14 proposed herein is designed neither with mechanical compliance nor with centre of motion, but relies on accurate resolved motion about a pivot point 206 determined by a specific procedure, and on real-time control of forces and torques applied to the effector unit 30 in order to optimise the location of the pivot point 206. Moreover, this feature gives the flexibility to translate the pivot point 206, if required by the surgeon S, in order to improve the intra-abdominal workspace. Another advantage is the capability to adapt to variations of the absolute location of the pivot point 206 due, for instance, to the loss of abdominal pressure.

As is apparent, the robot manipulator 14 should have certain motion capabilities in order to provide the effector unit 30 with a dexterity comparable to manual handling of laparoscopic instruments by surgeons. Based on the motion conditions given in Table 1, the preferred kinematic capabilities which have been found for the joints J1 to J6 in this specific example are summarized in Table 2. Roll, pitch and yaw angles can be defined relative to an absolute reference system, e.g. on the fulcrum.

TABLE 2

| Joint | Max Travel | Max Speed | Max Acceleration |
|---|---|---|---|
| J1 - Elevation | 700 mm | 600 mm/s | 4 m/s$^2$ |
| J2 - Shoulder | +/−90° | 60°/s | 400°/s$^2$ |
| J3 - Radial | 600 mm | 600 mm/s | 4 m/s$^2$ |
| J4 - Yaw | [−360° +360°] | 260°/s | 1900°/s$^2$ |
| J5 - Pitch | [−60° +180°] | 75°/s | 500°/s$^2$ |
| J6 - Roll | Infinite | 250°/s | 2400°/s$^2$ |

In terms of speed and acceleration capabilities for the respective joint, the values given in Table 1 are relatively high and therefore require strong actuators, a rigid structure of arm 26 and wrist 28 and an appropriated floor fixation by means of base 24. Obviously, lower values can be chosen which lead to reduced requirements, but this comes at the cost of reduced dynamics at the pivot point 206.

Another relevant aspect, especially in tele-operated robotic surgery with force reflection, is the accuracy requirement for the manipulator 14. Sufficient accuracy contributes to reducing stresses at the trocar incision, and allows to carry out precise force/torque compensation.

In the chosen design, the static accuracy of the manipulator 14 at the connection to effector unit 30, i.e. at the tool flange 32 (see FIG. 4) shall be better than ±2 mm for position and better than ±0.1° for orientation at the FRF (see FIG. 16). Herein an external load of 1.5 kg is assumed at the tip of a connected laparoscopic instrument 18 and the FRF is assumed at 280 mm from the axis of (R) joint J5. The dynamic accuracy shall be better than ±4 mm for position and ±0.5° for orientation at the FRF. These features are obtained, among others, through accurate mechanical machining of structural parts, stiffness of links L1-L6 and joints J1-J6, sufficient resolution of position sensors, proper tuning of PID motor control loops, kinematics calibration of the manipulator, etc.

In this context, the aforementioned absolute position sensors (e.g. 65, 88, 108, 148) provided at the output of each joint J1 to J6 provide the following advantages:

Homing the joints J1 to J6 of the robot manipulator 14 without actuating the joints; this means that the initial value of the incremental sensors used to control the motors, is provided by the absolute sensors. If absolute sensors were not available, a homing procedure could be implemented moving every joint in a giving direction to find a reference signal. No automated moves for homing at start-up ensures a fast set-up procedure and improved safety.

Real-time determination of position and orientation of the effector unit 30 avoiding joint elasticity errors caused by transmission mechanisms;

Monitoring deviations of the robot manipulator 14 from the FRF;

Detecting a joint transmission failure (e.g. belt rupture) or other hardware failure by monitoring data consistency using the positions indicated by the respective motor encoder provided at each joint J1-J6.

Another aspect in robotics is the mathematical model used to control the robot manipulator 14. Departing from a theoretical model of the robot manipulator 14, the effective and accurate "concrete" model, including parameters such as offsets to the kinematics arrangement, elasticity of joints J1 to J6, elasticity of links L1 to L7, actuators backlash and other linearity errors is necessarily determined during a calibration process. The identified "concrete" manipulator model is used for three purposes: firstly, to improve accuracy of the robot manipulator 14 using the theoretical model in the motion controller (which simplifies the inverse kinematics calculation) with real joints offsets and links lengths; secondly, to accurately compute, in real time through forwards formulation, the position and orientation of the 6-DOF FTAS 122 and the loads attached, (these values are required for compensating gravitational and acceleration loads); thirdly, to determine, in real time through forwards formulation, the position and orientation of the instrument tip and deduce parameters required for forcereflection (e.g. the penetration of the instrument 18).

The following paragraphs give a more detailed description of the laparoscopic instrument actuator (LIA) 120.

As seen in FIGS. 14 and 15, the LIA 120 forms part of the effector unit 30. The LIA 120 provides a generic actuation interface for using standard laparoscopic instruments such as grasping/dissecting forceps, scissors, suction/irrigation tools, etc. with the robot manipulator 14. Hence, the LIA 120 forms the extremity the manipulator 14 and represents its hand part since it reproduces the actions of a surgeon hand. The LIA 120 comprises a housing 154 the rear end of which forms an interface flange 156 for connection to the FTAS 122 whereas its front end forms the extremity of the robot manipulator 14. In a different configuration of an effector unit, a LIA could include joint J6. This configuration requires however a more complex mechanical design of the instrument adaptor that shall include a rotation mechanism together with the open-close mechanism and power-transmission. In addition, the sterile field should be maintained even with the rotation mechanism.

The LIA 120 shown in FIGS. 14-15 and FIGS. 18-22 is adapted for use with any standard laparoscopic instrument that can be divided into a handle on one side, and a stem on the other side. Herein the stem is defined as comparatively thin elongated tube having at its tip, for example, forceps/scissor jaws inserts, suction/irrigation means, basic tools like a knife or an electric cautery/cutting device. The end opposed to the tip comprises a socket which is designed to connect the stem to the handle for the surgeon.

Compatibility of the robot manipulator 14 with standard instruments is achieved by the design of the LIA 120 and the design of corresponding instrument stem adaptors, in the following referred to by the acronym ISA, of which an example is shown in partial sectional view in FIG. 17.

Figure 17:
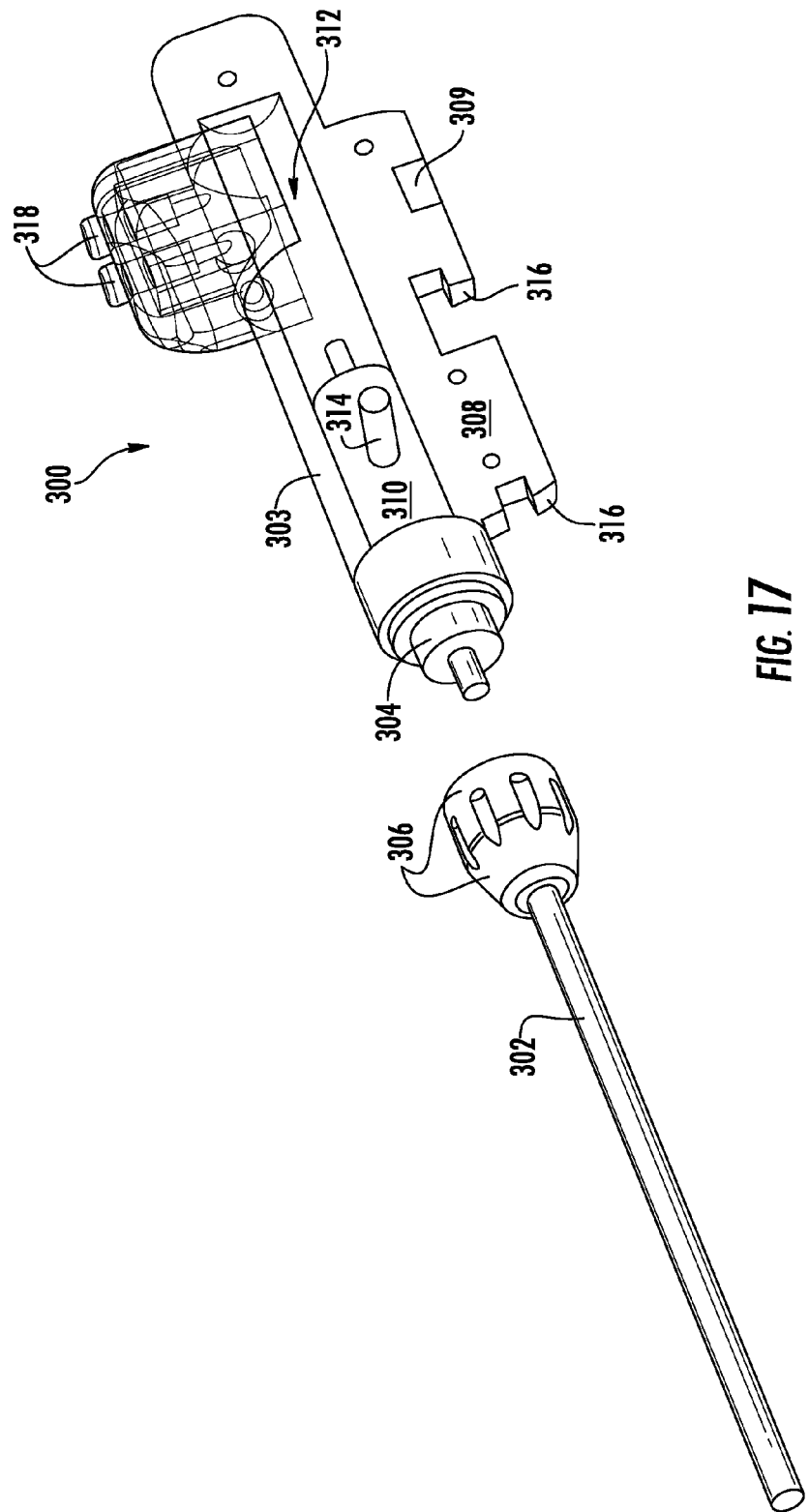
FIG. 17: is a perspective view of an instrument stem adaptor (ISA) and a corresponding instrument stem.

FIG. 17 shows the ISA (instrument stem adaptor) 300 to which an instrument stem 302 can be connected. The ISA 300 is connectable to the LIA 120 by mounting it into the seat 130 shown in FIG. 15. To this effect, the ISA 300 comprises a case 303 with an essentially cylindrical outer surface. As seen in FIG. 17, the ISA 300 is designed as a coupling element between the instrument stem 302 of a conventional (laparoscopic) instrument, and the LIA 120. To this effect, the ISA 300 comprises a stem connector 304 at its front end. The stem connector 304 is designed for connection to a specific type socket 306 of the stem 302, which depends on the actual instrument. Originally, the socket 306 is designed for connection to a laparoscopic instrument handle (not shown). As seen in FIG. 17, the stem connector 304 reproduces the connector of the original handle for which the stem 302 was designed. The ISA 300 further comprises as coupling means a coupling member 308 for secure connection to the LIA 120. The coupling member 308 is arranged laterally on the case 303 and protrudes radially there from so as to block rotation of the ISA 300 when it is mounted to the LIA 120. A small metallic block 309 is included in the coupling member 308 in order to provide a metallic detection surface for an inductive presence switch (cf. part 404 described below) of the LIA 120. A linearly slideable piston 310 is arranged in a cylindrical guide 312 internal to the ISA 300. A cylindrical slider pin 314 is attached transversely to the piston 310 and protrudes out of the case 303 for operating the piston 310. Sliding operation of the piston 310 actuates a rod inside the instrument stem 302 for operating the tool at the tip of the instrument stem 302. As will be appreciated, the ISA 300 reproduces the functionality of the handle originally connected to the stem 302 as regard operating the instrument stem 302, while providing together with the LIA 120 a connection interface to the robot manipulator 14.

It will be understood that the specific embodiment of the ISA 300 shown in FIG. 17 is designed for an instrument requiring mechanical actuation such as an open/close function for the instrument tip, for example, scissors and graspers with or without unipolar or bipolar electric power transmission. A variety of other types of analogous adaptors are also encompassed by the present disclosure, each adaptor being adapted to a specific type of laparoscopic instrument, i.e. a specific type of stem (e.g. 302), which is to be connected to the LIA 120. Accordingly, the ISA comprises, depending on the requirements of the instrument, a linear slider pin 314 e.g. for actuation of the jaws of the instrument, one or more electrical connectors 318, e.g. for unipolar or bipolar cautery power, etc, and/or one or more conduit connection(s), e.g. for irrigation or suction instruments. Although shown in FIG. 17 with electrical connectors 318, it will be understood that for a purely mechanical instrument 18, the parts of the ISA 300 forming the electrical connectors 18 (drawn in thin line width in FIG. 17) need not be provided. It may be noted that the constituent material of any type of ISA shall be chosen such that it can be sterilized e.g. through a steam autoclave. In fact, by virtue of the design of the LIA 120, the ISA is the only part of the robotic surgical system 10 that needs to be sterilized (besides the instrument stem of course). During operation, the housing 154 of the LIA 120 and the other parts of the effector unit 30 are enclosed in a sterile plastic bag. Although not shown, it is apparent that, for mechanically non-actuated but electrically powered instruments such as electro-bistouries or knifes, the ISA does not need to have the slider pin 314 and an associated mechanical transmission. For instruments such as an irrigation or suction canula, the ISA is equipped with two tubes that are remotely commanded through electro-valves electrically actuated by the robot control system.

Figure 18:
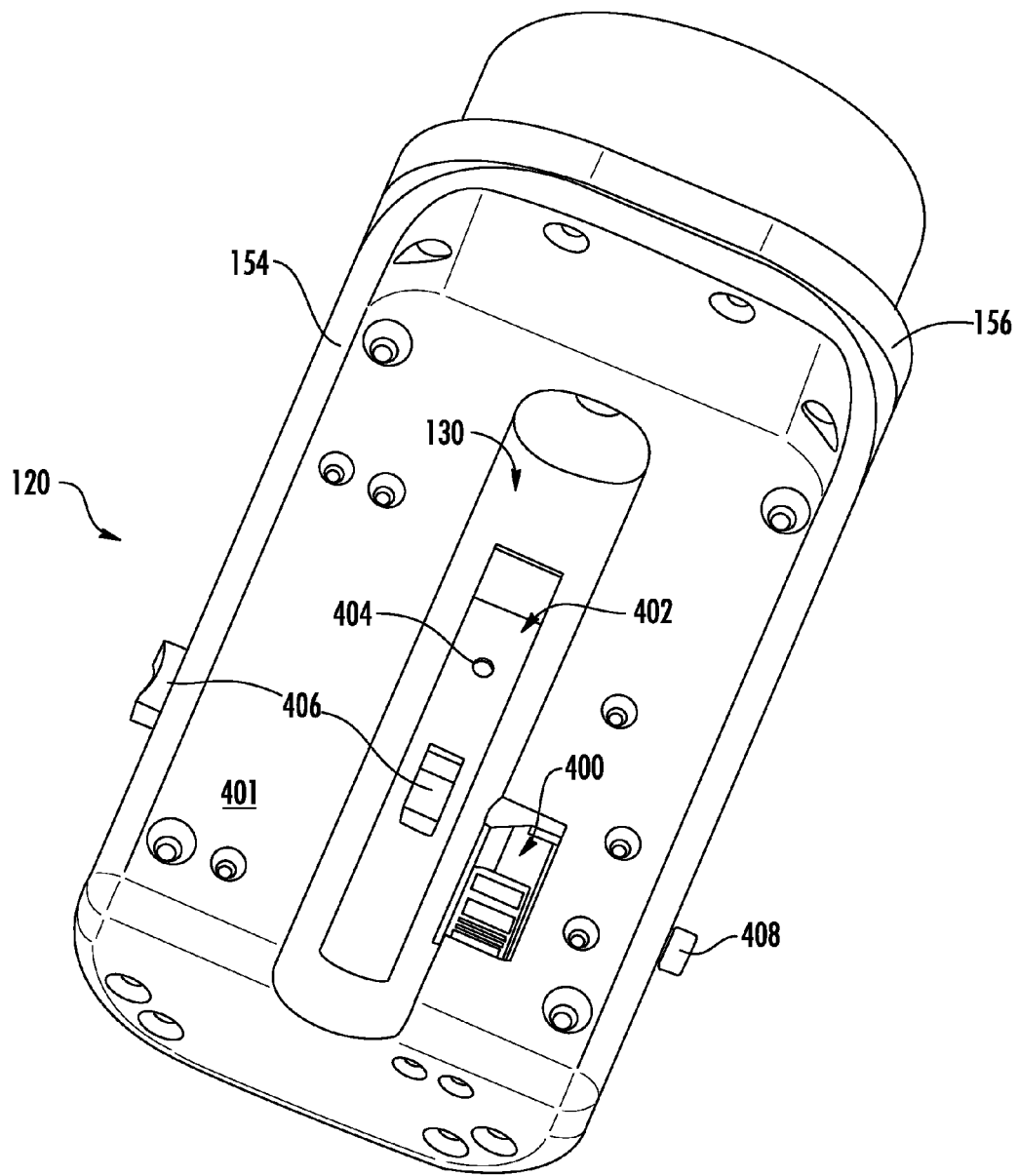
FIG. 18: is an enlarged perspective view of a laparoscopic instrument actuator (LIA) as shown in FIG. 14.

The LIA 120 shown in FIG. 18 is designed lightweight (e.g. less than 800 g of total weight) and so as to fit into a relatively small cylindrical envelope of about 90 mm or preferably 75 mm of diameter to increase the available workspace of two adjacent tools with nearby access ports 20. The total length of the LIA 120 (about 130 mm in a specific example) is mainly determined by the length of the ISA 300. The length of the LIA 120 is minimised in order to limit the distance between the rotation axis of the joint J5 and the pivot point 206 of the FRF (see FIG. 17). In fact, this distance offset is determining for the travel range and speed/acceleration capabilities of all manipulator joints J1 to J5. It is however recommended that the length of the LIA 120 be at least 6 cm in order to allow gripping the LIA 120 by hand in manual mode (i.e. using the housing 154 connected to the FTAS 122 as a "joystick").

As seen in FIG. 18, the outer surface of the housing 154 has smoothed edges. It is made of an easily cleanable, lightweight and non-conductive material. Moreover, the LIA 120 has a partially rotationally symmetric design with respect to the stem 302 of an adapted instrument 18 mounted using an ISA 300. When the ISA 300 is properly connected to the LIA 120, the axis of the stem 302 coincides with the roll axis of joint J6 and with the normal axis of the FTAS 122.

As further seen in FIG. 18, the housing 154 of the LIA 120 comprises a linear actuation mechanism 400 for actuating a mounted instrument 18 by means of the ISA 300 as will be detailed below. The seat 130 is formed as a concave elongated semi-cylindrical recess in an access surface 401 of the LIA 120 to facilitate insertion and extraction of the ISA 300. The seat 130 for receiving the ISA 300 is approximately coaxial to the rotation axis of the joint J6 and extends along the central axis of the housing 154. As will be appreciated, the mounting and removing direction of the ISA 300 with respect to the LIA 120 is radial relative to the rotation axis of the joint J6. The LIA 120 is configured such that the seat 130 is accessible from the entire half plane above the access surface 401. As seen in FIG. 18, the seat 130 comprises a longitudinal groove 402 which deepens the seat 130 radially into the body of the LIA 120. The additional groove 402 is configured for receiving the coupling member 308 of the ISA 300. The engaging part of a locking mechanism 406 associated to the seat 130 is arranged in the groove 402 and cooperates with the coupling member 308. The seat 130 is formed as a semi-cylindrical recess with a rounded end portion conformed to the outer cylindrical shape of the case 303 of the ISA 300. A presence detector 404, e.g. an inductive presence switch, is arranged in the seat 130 for presence detection of the ISA 300 by sensing the metallic block 309 (see FIG. 17). A dead-man switch button 408 allows switching the control system of the robot manipulator 14 to manual mode. In manual mode, the LIA 120 (and, if connected, the instrument 18) is positioned and oriented by the robot manipulator 14 using the information produced by the assistant handling the housing 154 of the LIA 120 and read by the FTAS 122. Manual mode is particularly useful for inserting or extracting an instrument through a trocar.

Figure 19:
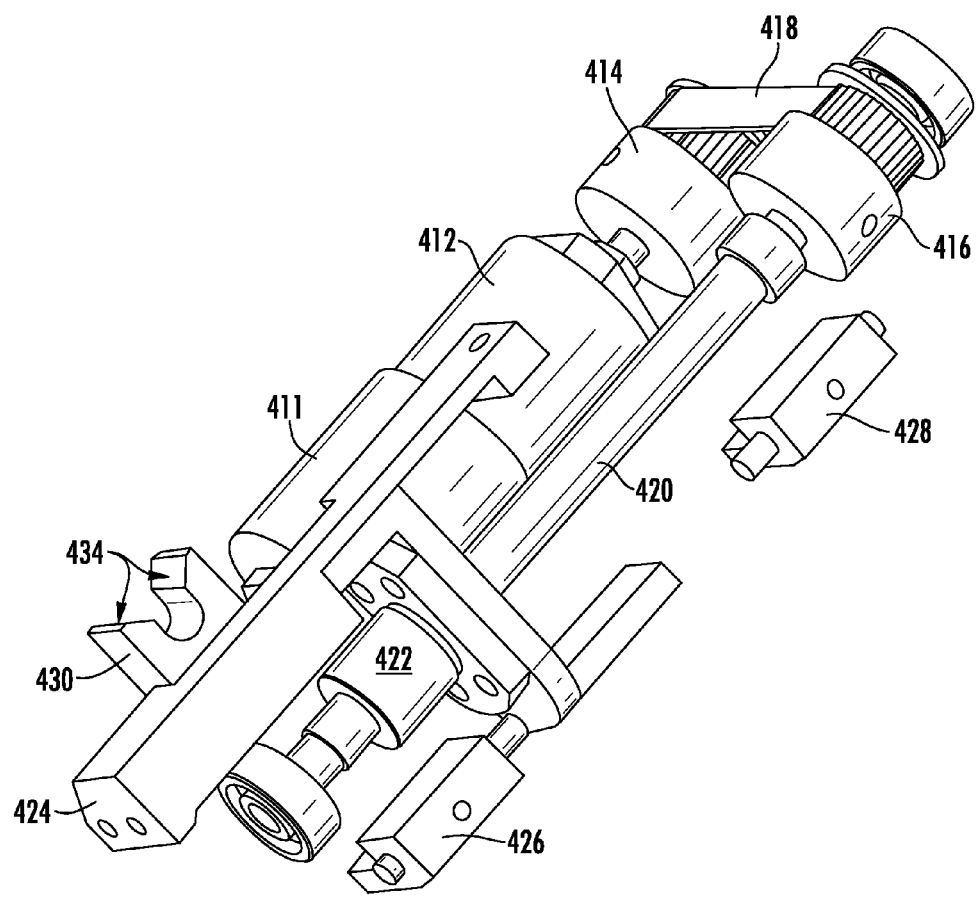
FIG. 19: is a perspective view of a drive assembly in the LIA of FIG. 18.
Figure 20:
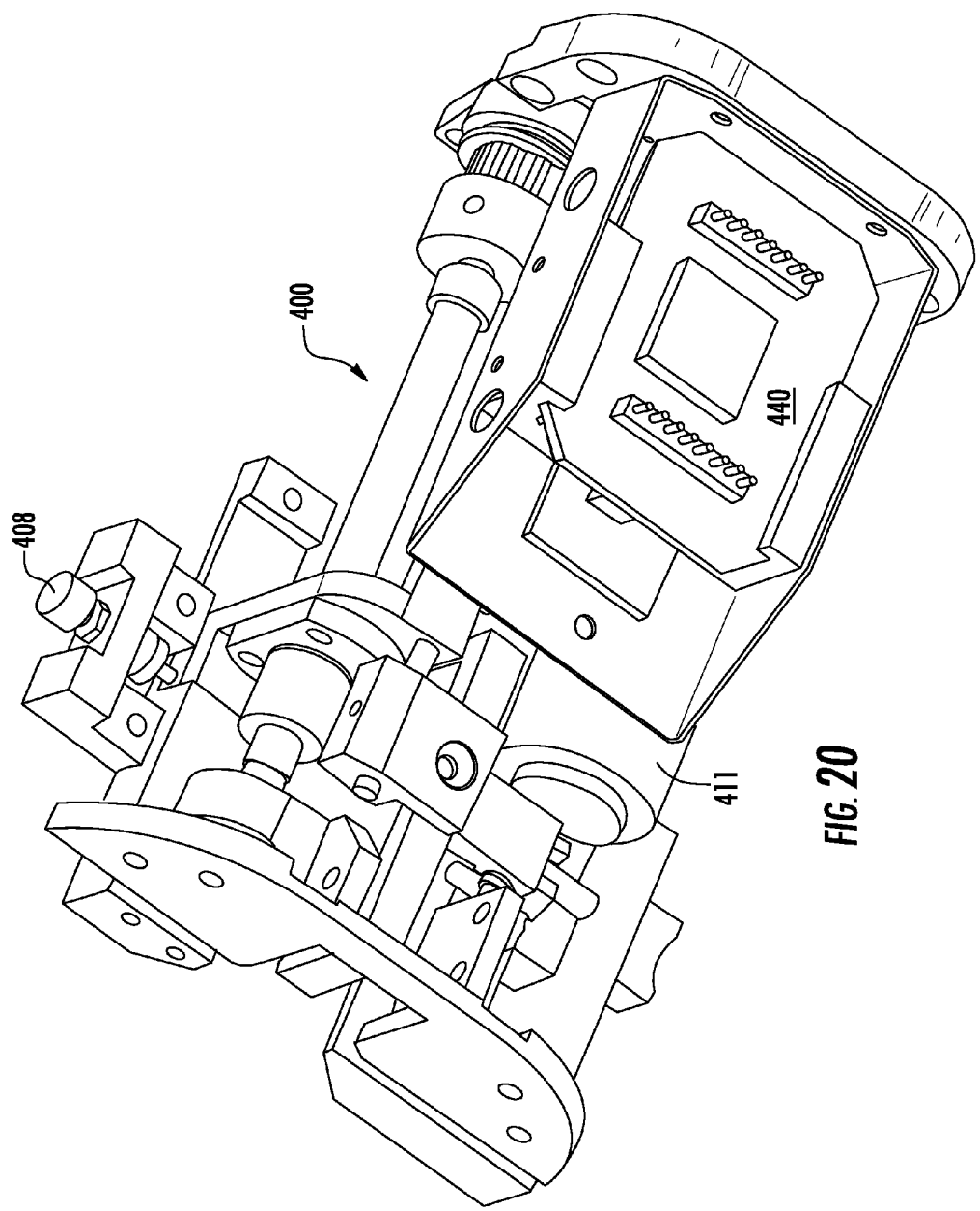
FIG. 20: is a perspective view from underneath showing further internal components of the LIA shown in FIG. 18.

Details of the linear actuation mechanism 400 are best seen in FIG. 20. The actuation mechanism 400 comprises a miniature brushless motor 411 connected via a gearbox 412 and pulleys 414 and 416, which are coupled by a belt 418, to a ball-screw 420. The ball screw 420 cooperates with a nut 422 arranged thereon so as to transform rotation into linear motion as seen in FIG. 19. The nut 422 is guided by a linear guide 424 in order to reduce transversal efforts on the ball-screw 420. Inductive limit switches 426 and 428 are placed at the end-of-travel locations of the nut 422 and connected to a control unit for limiting travel of the actuation mechanism 400.

As seen in FIG. 19, the actuation mechanism 400 communicates linear motion to a slider carriage 430 of the LIA 120, as will be detailed below. In a preferred embodiment, the following parameters were chosen for the actuation mechanism 400:

maximum mechanical travel of the slider carriage 430: 7 mm (normally 5 mm are sufficient for standard instruments, but it has been found that several stems of the same type may have travel lengths varying by up to 2 mm);

travel speed range: from 1 mm/sec to 20 mm/sec;

maximum actuation force: 200 N;

Stepper motors are preferably avoided in the LIA 120 because they produce vibrations that would be a considerable source of noise for the FTAS 122. Therefore, a miniature brushless motor 411 equipped with a shaft position encoder is used. Such motors are available e.g. from Faulhaber GmbH, Schoenaich, Germany. Other non-vibrating linear motion mechanisms such as cable-driven transmission are however not excluded.

FIG. 20 shows a power and control unit 440 for the motor 411 which is embedded in the housing 154 of the LIA 120 and supplied e.g. with 24 VDC power. In order to further reduce the diameter of the housing 154, the power and control unit 440 may be placed in an additional housing either between the flange 156 and the FTAS 122, or between the FTAS 122 and a connection flange to the joint J6 (not shown), or inside the cover 124 of the joint J6, e.g. behind the slip-ring collector 80 close to the motor 141. The power and control unit 440 is designed inter alia for actuating the slider carriage 430 with a given speed profile according to received position commands, for limiting motor current on user demand, for managing motion based on signals from limit switches 426, 428, for homing the motor 411 using a limit switch, and for monitoring the presence detector 404 on the housing 154. Other safety functions, e.g. emergencystop functions, are also implemented using a servo error of the motor 411, i.e. target position minus effective position, and thermal protection of the motor 411. In order to reduce required space for the LIA 120, the linear actuation mechanism 400 is not equipped with an absolute position sensor. Nevertheless, an automated homing procedure is ensured by using limit switches 426 and 428 as home sensors. During operation, the absolute position of the slider carriage 430 can be periodically recorded, e.g. in a suitable memory of the robot control system, for fast recovery of the system after a power shutdown or failure. Presence of the ISA 300, i.e. whether it is correctly mounted to the LIA 120, is sensed through the inductive presence switch 404 (see FIG. 18) arranged in the seat 130. The output of the inductive presence switch 404 is fed to an available input of the control unit 440.

As best seen in FIGS. 17 and 19, the slider carriage 430 of the actuation mechanism 400 is adapted to receive the slider pin 314 of the ISA 300. By action of the motor 411, the slider carriage 430 is repositioned so as to drive the slider pin 314 of a connected ISA 300. The slider pin 314 in turn actuates the piston 310 to operate a working element or tool at the tip of the stem 302 (not shown), e.g. a jaw open/close mechanism. In other words, the combination of linear actuation mechanism 400 and ISA 300 simulates action of the handle which has been removed from the stem 302 and replaced by the ISA 300. Insertion of the slider pin 314 into the slider carriage 430 is facilitated by bevelled guiding surfaces 434.

Figure 21:
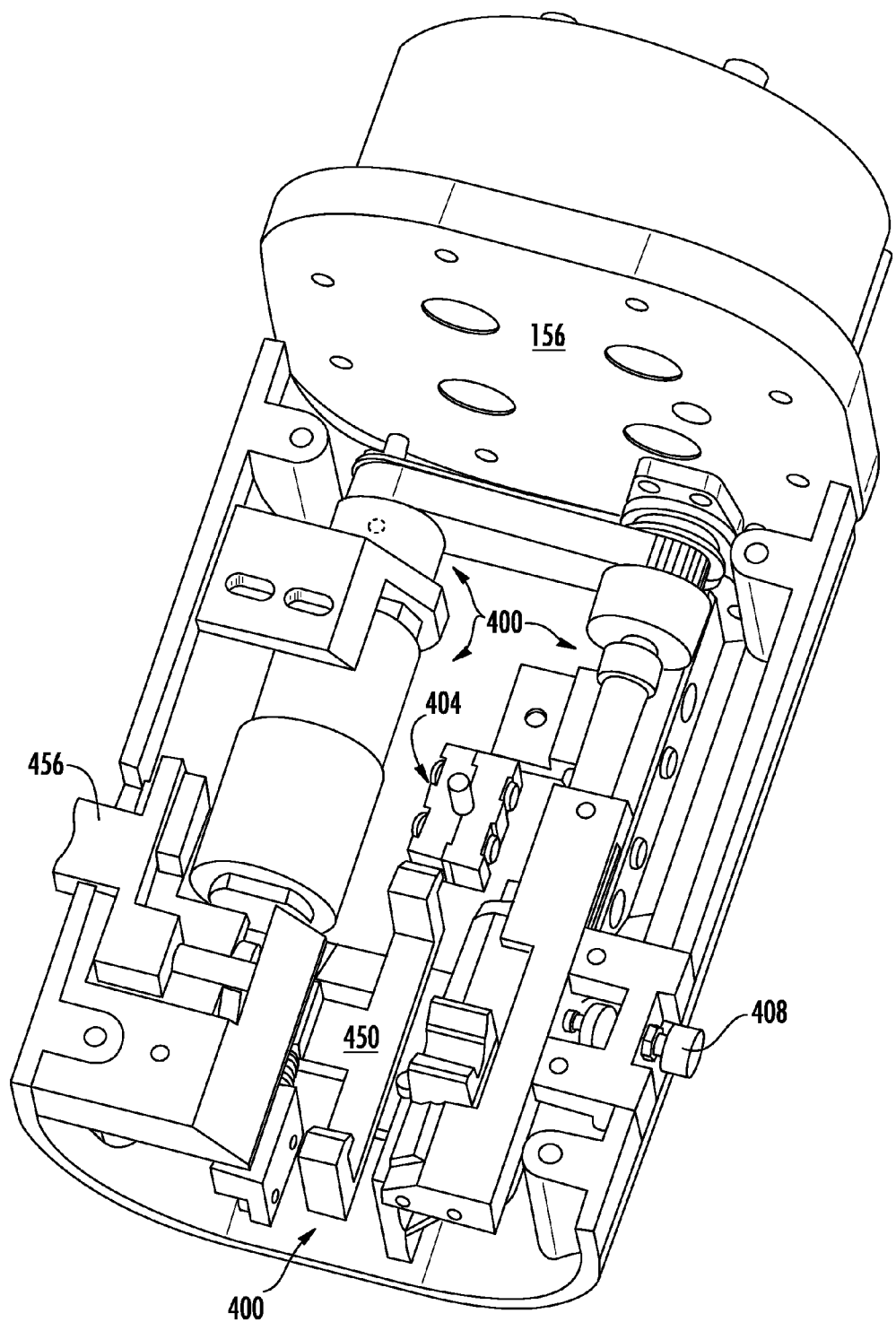
FIG. 21: is a perspective view from above showing further internal components of the LIA shown in FIG. 18.
Figure 22:
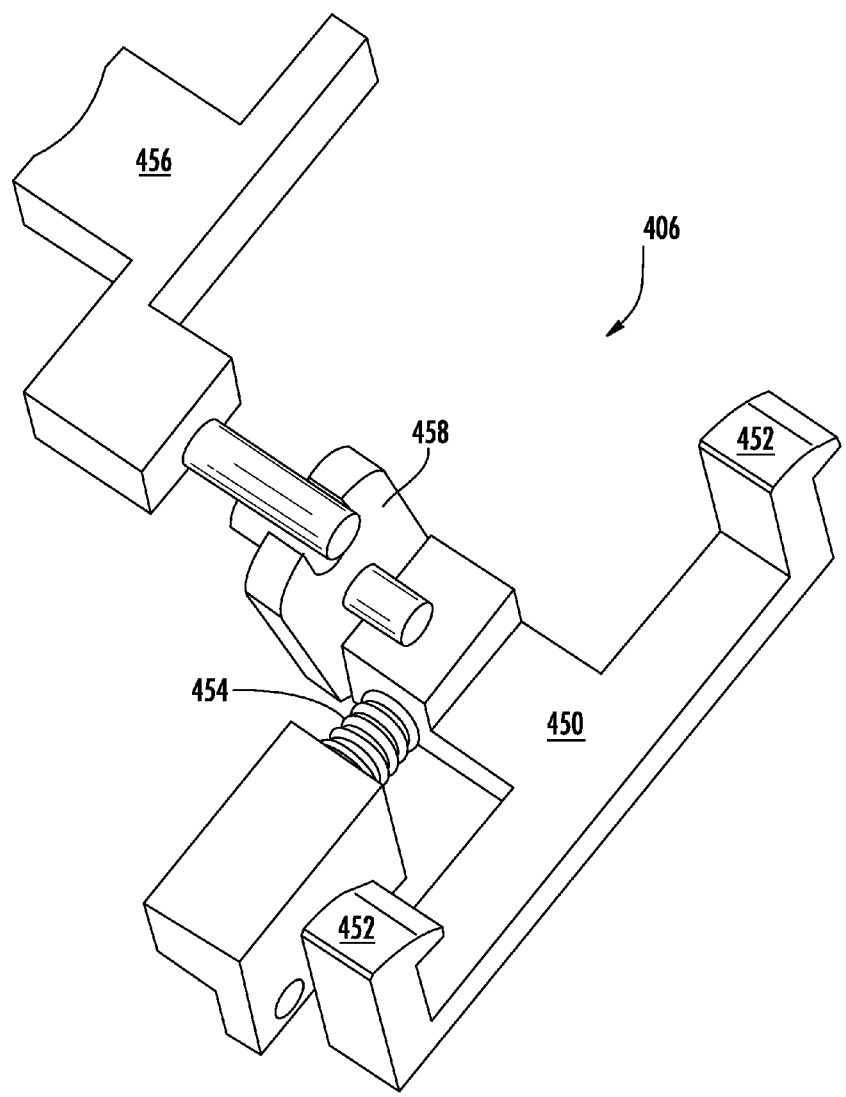
FIG. 22: is a perspective view showing a coupling mechanism used in the LIA shown in FIG. 18.

FIG. 21 and FIG. 22 show in more detail the configuration of the locking mechanism 406 of the LIA 120 only partially shown in FIG. 18. The locking mechanism 406 is configured as latch and comprises a slideable catch 450 arranged in the groove 402 (shown in FIG. 18) of the seat 130. It will be understood that the catch 450 is guided by suitable means in the groove 402. The groove 402, together with the slideable catch 450, are configured for engagingly receiving the coupling member 308 of the ISA 300 shown in FIG. 17. The catch 450 comprises two noses 452 for engaging two protrusions 316 formed by slots in the coupling member 308 (see FIG. 17). The edges of the coupling member 308 are rounded to ease insertion and removal in/from the groove 402.

The design of the catch 450 is best seen in FIG. 22. A spring 454 resiliently urges the catch 405 towards the FTAS 122. A linearly guided knob 456 allows to rotate a pivot 458 which is coupled to the linearly guided catch 450 in order to manually disengage the catch 450 from the coupling member 308 when the ISA 300 is to be removed. The noses 452 of the catch 450 are bevelled so as to allow insertion of the ISA 300 simply by pushing. The engaging portions of the noses 452 and the protrusions 316 are rounded according to a conjugated profile in order to limit damages to a sterile plastic sheet used for covering the LIA 120. As will be understood, other equivalent coupling or locking mechanisms could also be used, for example using permanent magnets installed in the LIA with metallic plates and a cam-based lever mounted on the ISA to replace the latch mechanism. It is preferred that the fixation mechanism, e.g. the locking mechanism 406 and coupling member 308, is designed to ensure that the ISA 300, when mounted to the LIA 120, can resist to the following forces and moments without disconnecting from the LIA 120:

traction and compression forces of 100 N;
  torsion moments corresponding to radial forces of 15N at the instrument tip;
  bending moments of up to 5 Nm.

It will be appreciated that the LIA 120 and each cooperating ISA (e.g. 300) are designed for fast and easy manual installation and removal of an adapted laparoscopic instrument 18, i.e. a stem (e.g. 302) assembled with an ISA (e.g. 300), by the surgeon assistant A. The essentially cylindrical outer shape of the ISA 300, its coupling member 308, the seat 130, the groove 402 and the locking mechanism 406 as described above provide guided insertion and a simple connecting procedure of the ISA 300 to the LIA 120. The design ensures the required stiffness when the ISA is inserted and a simple extraction procedure by means of a few manual moves. By means of this design, insertion and extraction of the adapted instrument 18 (i.e. stem and ISA) can be carried out essentially as fast as in manual surgical operations, where the assistant replaces a conventional instrument for the surgeon in about 6-9 seconds.

It should be noted that insertion or removal of an adapted instrument 18 comprising the ISA (e.g. 300) and the stem (e.g. 302) can be done safely in both cases, when the instrument is outside the body of patient P or when the instrument is inserted in the body of patient P. It is also possible to carry out removal while the slider pin 314 is driven.

Before mounting the adapted instrument to the LIA 120, a number of preliminary conditions should be met. Firstly, if the instrument is partially inserted in the trocar (without exceeding the trocar length), the LIA 120 should previously be positioned and oriented by the manipulator 14 into a taught position that aligns the rotation axis of the effector unit 30 (joint J6) with the trocar. Secondly, the slider carriage 430 should be placed into the "insertion reference position" by the robot control system, e.g. a position closest to the interface flange 156. When an ISA (e.g. 300) is removed, the slider carriage 430 should be automatically moved into this "insertion reference position" by the robot control system. As mentioned above, presence, absence or abnormal release of an ISA can be detected by the presence detector 404. Thirdly and if present, the slider pin (e.g. 314) of the ISA (e.g. 300) should be in an "insertion reference position" corresponding to that of the slider carriage 430. This position of the slider pin 314 is preferably defined such that instrument is in "closed" configuration, for example, the jaws of a forceps/scissor instrument are loosely but sufficiently closed in this position. As best illustrated by FIG. 14, the insertion procedure of an adapted laparoscopic instrument 18 including an ISA (e.g. 300) and a stem (e.g. 302) can be carried out by only one simple manual move according to arrow 460 consisting of placing the ISA (e.g. 300) on its seat 130 and of slightly pushing on the ISA along the same direction to engage the coupling member 308 with the locking mechanism 406. The presence detector 404 gives an affirmative output when the coupling member 308 is correctly installed in the groove 402. During this insertion procedure, the slider carriage 430 engages the slider pin 314 without the need for further measures, if the aforementioned conditions have been met.

When the surgeon S requests an instrument change through his master console 15, four operations are normally carried out automatically by the robot control system. Firstly, the robot control system controls the instrument 18 to release any tissue. Secondly, it moves the instrument near the trocar port following the instrument axis direction. Thirdly, the tool tip, e.g. the instrument jaws, are brought into a configuration which avoids hooking of the tip at the trocar. Fourthly, it releases the motor of joint J6 such that the surgeon assistant A can freely rotate the LIA 120 to facilitate removal of the instrument from the LIA 120. After these operations, removal of an adapted laparoscopic instrument 18 can be carried out safely in two simple moves and at any time.

The first extraction move consists of pushing the knob 456 so as to unlock the locking mechanism 406. The second extraction move consists of pivoting the ISA (e.g. 300) and the stem (e.g. 302) about the tip of the stem by rotation about an axis perpendicular to the stem axis so as to remove both from the seat 130 and subsequently, if still inserted, so as to extract the stem (e.g. 302) from the body of patient P.

As is apparent from the above insertion and removal procedures, the design of the LIA 120 and ISA (e.g. 300), enables instrument insertion or extraction even when the stem (e.g. 302) of an adapted instrument 18 is still partially inserted in the body of patient P through the trocar 200 (see FIG. 16). As will be appreciated, the moves required for extraction are not in the penetration direction with respect to the patient P since they consist of a pivoting move perpendicular to the longitudinal axis of the seat 130 and a subsequent extraction move. Moreover, in case a move in a given pivoting direction could harm the patient, this direction can be changed by rotating the LIA 120 by hand LIA through joint J6. In addition, in case of power failure, an ISA (e.g. 300) together with its stem (e.g. 302) can be released and extracted manually.

With respect to the LIA 120 as described above, it will be appreciated that a wide variety of existing standard laparoscopic instruments can be used in the robotic system 10 by means of simple instrument stem adaptors (ISA) (e.g. 300). The LIA 120 in combination with a corresponding ISA replaces the handle part of a given laparoscopic instrument without loss of actuation or power supply capability. The LIA 120 is generically designed i.e. independent from the type of instrument that is to be coupled to the robot manipulator 14. Hence, only the ISA (e.g. 300) needs to be designed specifically in accordance with the instrument requirements. As described above, the LIA 120 is capable of providing inter alia the following functions:
"open/close" actuation of instrument tool tips, e.g. of instrument jaws, using the linear actuation mechanism 400;
adapting the required "open/close" travel length for every type of instrument;
handling non-actuated instruments like knives through action of the robot manipulator 14.

Furthermore, the LIA 120 permits beneficial cost-effectiveness in robotic laparoscopy because of several factors. Firstly, as opposed to prior art devices which require several actuators per manipulator because the instrument and the associated actuator are assembled as single unit in a single enclosure, only one LIA 120 is needed for each manipulator 14. This allows savings inter alia on actuator costs. Secondly, instrument costs are reduced by using the stems (e.g. 302) of standard laparoscopic instruments and a corresponding instrument stem adaptors (e.g. 300) of simple construction. Therefore, the cost of an adapted instrument 18 for use with the LIA 120 is almost identical to the cost of a standard manual laparoscopic instrument (i.e. including the handle). Thirdly, instrument maintenance costs are essentially equal to those for standard laparoscopic instruments because the ISA (e.g. 300) design is robust against sterilization cycles.

Figure 25:
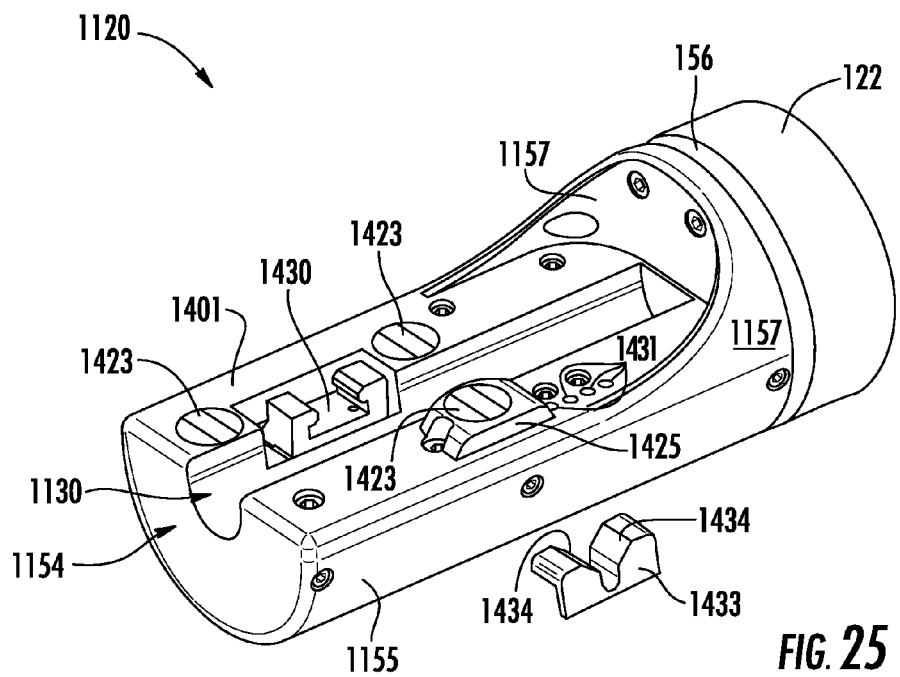
FIG. 25: is a perspective view of an alternative embodiment of a laparoscopic instrument actuator (LIA) for use in the effector unit shown in FIG. 14.

Turning to FIG. 25, an alternative embodiment of a LIA 1120 will be described. Since many aspects and advantages of the LIA described herein above also apply to the LIA 1120, only the main features and differences will be detailed hereinafter.

The LIA 1120 shown in FIG. 25 has a semi-cylindrical housing 1154 that has an upper substantially flat access surface 1401 for facilitating mounting and removing of an ISA to the LIA 1120. The opposite surface 1155 of housing 1154 is semi-cylindrical in conformity with a cylindrical envelope that is coaxial to the rotation axis of J6. The diameter of the semi-cylindrical surface 1155 is chosen ergonomically to allow handling by a human operator, e.g. in the range of 50-135 mm, preferably of about 90 mm, especially for commanding the robot manipulator 14 in the manual mode mentioned above. Since the semi-cylindrical housing has a substantially smaller cross-section than the interface flange 156 by means of which the LIA 1120 is attached to the FTAS 122, the housing 1154 further includes gradual reinforcing ribs 1157. The reinforcing ribs have a gradual i.e. smoothly growing shape starting from access surface 1401 up to the upper edge of the interface flange 156. The reinforcing ribs 1157 are further curved in conformity with the cylindrical envelope of the semi-cylindrical surface 1155. The reinforcing ribs 1157 connect the access surface 1401 to the interface flange 156 and thereby reinforce and increase the rigidity of attachment of the housing 1154 to the interface flange 156. Thereby the reinforcing ribs 1157 ensure a more accurate transmission of forces and torques from an ISA via the LIA 1120 to the FTAS 122. It may be noted that similar reinforcing ribs are also provided in the LIA 120 of FIG. 14.

FIG. 25 further shows an alternative coupling mechanism for mounting an instrument stem adaptor to the LIA 1120 and thereby to the effector unit 30. In the LIA 1120, as in the LIA 120, a seat 1130 is formed as a concave elongated semi-cylindrical recess in the access surface 1401 to provide self-centering of an adaptor on the rotation axis of J6. Furthermore, the coupling mechanism comprises a plurality of magnetic devices 1423, two on the side of the slider carriage 1430 and one on the other side of the seat 1130, the latter one being arranged on an elevation 1425 off the access surface 1401. The elevation 1425 provides an additional retaining constraint in axial direction to a mounted adaptor and permits self-adjusted positioning in axial direction of the adaptor by slopes towards the access surface 1401. As will be understood, the magnetic devices 1423, which can be electromagnets, permanent magnets or a combination of both, ensure fastening of a correspondingly designed ISA by means of magnetic attraction. Avoiding a mechanical snap-in attachment eliminates the risk of damage to a sterile plastic cover used to wrap up the manipulator 14 or at least the effector unit 30.

FIG. 25 illustrates a plurality of inductive presence sensors 1431 for identifying an instrument mounted to the effector unit 30 by means of an inductively identifiable material pattern provided on an ISA. Four inductive presence sensors 1431 are arranged in a row and allow to distinguish and identify 16 instrument types when using a binary code (4 bit word) based on the presence or absence of conductive material in a row of corresponding locations on the ISA facing the inductive presence sensors 1431. Furthermore, the inductive presence sensors 1431 also allow for presence detection if the pattern code (4 bit word) corresponding to an absent instrument is used for this purpose, i.e. when no conductive material faces any inductive sensor 1431.

An engagement member 1433 is separately shown in FIG. 25. The engagement member 1433 is part of the actuation mechanism which includes the slider carriage 1430 and has bevelled capture surfaces 1434 leading into a slit for engaging the slider pin 314 of an ISA. The bevelled surfaces 1434 facilitate insertion of the slider pin 314 of an ISA. As will be appreciated, the engagement member 1433 is detachable from the slider carriage 1430 and made of sterilization compatible material. The engagement member can thereby be installed on the carriage 1430 only after a sterile wrap covers the LIA 1120. Since the motion range of the carriage 1430 is limited, no damage to the sterile wrap can occur.

Figure 26:
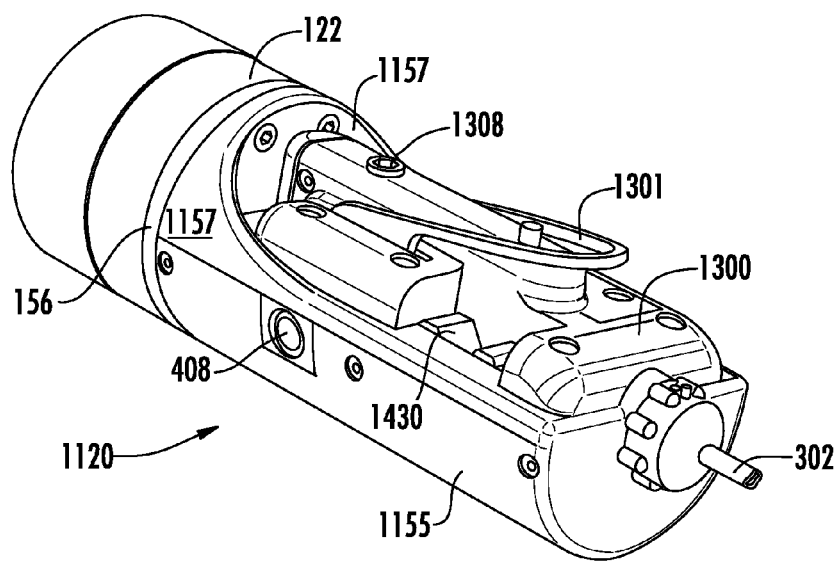
FIG. 26: is a perspective view of the LIA of FIG. 24 with an alternative embodiment of an instrument stem adaptor (ISA) connected to the LIA.

FIG. 26 shows an alternative embodiment of an ISA 1300 mounted to the LIA 1120 of FIG. 25. The ISA 1300 is designed to be compatible with the alternative design of LIA 1120 and will be detailed hereinafter. The ISA 1300 is dimensioned such that its base is confined to the access surface 1401. The function of the ISA 1300 is the same as that of the ISA 300 shown in FIG. 17, namely to provide an interface allowing the use of stems 302 of standard manual laparoscopic instruments on the robot manipulator 14 without loss of any functionality available in manual interventions. FIG. 26 also shows a switch button 408 provided on the LIA 1120 for switching the system to manual mode. The ISA 1300 is provided with a lever 1301 for easy manual demounting i.e. separating the ISA 1300 from the LIA 1120. The ISA 1300 also has an electrical connector 1308 for connecting powered instruments (e.g. coagulation or cutting instruments) directly to an electrical power source without wires passing through the LIA 1120.

As is apparent from FIGS. 25 and 26, the design is such that all components of the LIA 1120, including the housing 1154, the flange 156, the reinforcing ribs 1157, the FTAS 122 sensor assembly and all parts of the mounted ISA 1300, including lever 1301 are located within the cylindrical envelope defined by the semi-cylindrical surface 1155. This is to reduce the risk of collision and damage when the LIA 1120 is rotated by J6.

Figure 27:
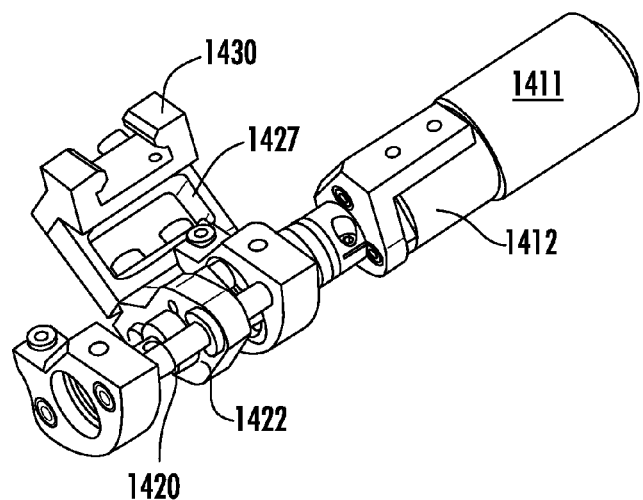
FIG. 27: is a perspective view of an alternative drive assembly used in the LIA of FIG. 24.

FIG. 27 shows an alternative actuation mechanism 1400 for communicating linear motion to the slider carriage 1430, differing in design from the mechanism of FIG. 19. It comprises a miniature brushless motor 1411 connected via gearbox 1412 and a ball screw or worm gear 1420 to a nut member 1422. The carriage 1430 is fixed to the nut member 1422 via the intermediate of a force sensor 1427. The force sensor 1427 allows to measure forces exerted by the carriage 1430 onto the slider pin 314 and viceversa. It will also be appreciated that the by virtue of mounting the slider carriage 1430 to the side of the longitudinal seat 1130, the motor 1411 and connected gears can be arranged in parallel to the longitudinal axis of ISA 1300 and stem 302. This allows minimizing the total length of the LIA 1120 whereby the requirements on actuator dynamics for certain joints (e.g. J4) are reduced. Furthermore, it will be appreciated that this actuation mechanism 1400 is optimized with respect to producing detrimental vibration. Other aspects and advantages of the drive mechanism 1400 are similar to those of the mechanism 400 described herein before.

Figure 28:
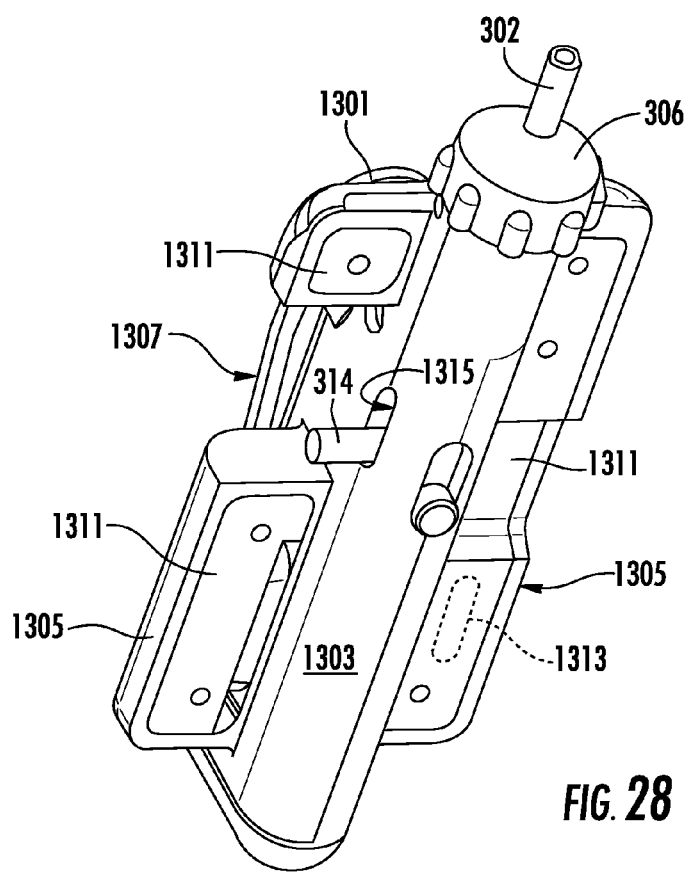
FIG. 28: is another perspective view of the ISA shown in FIG. 26.

FIG. 28 shows the underneath side of the ISA 1300 of FIG. 26 when detached from the LIA 1120. The ISA 1300 comprises an elongated case 1303 with a stem connector 1304 at its front end (see FIG. 30). The stem connector 1304 enables removable connection to a type socket 306 fixed to the stem 302 (only partly shown) of a standard manual laparoscopic instrument as long as any type of detachable connection is provided. Of course, connector and socket could respectively be located on stem and ISA. Similar to the case 303, the case 1303 has a semi-cylindrical surface on its underneath side for cooperation with the seat 1130. As seen in FIG. 28, lateral wings 1305 protrude from either side of the case 1303. The lateral wings 1305 have a flat lower surface that is conjugated to the access surface 1401 on the LIA 1120 (e.g. also to the elevation 1425). A cut out space 1307 is provided in one wing 1305 above the slider pin 314 for providing visibility and access, e.g. for manually moving the slider pin 314 when the ISA 1300 is coupled to the LIA 1120. FIG. 28 also shows flat ferromagnetic elements 1311 arranged in each wing 1305 on either side of case 1303. The ferromagnetic elements 1311 form coupling means that cooperate respectively with a corresponding magnetic device 1423 on the LIA 1120 as shown in FIG. 25. In the region 1313, an inductively identifiable pattern is provided on the ISA 1300 for identifying, by means of the inductive sensors 1431 shown in FIG. 25, the instrument that is used. In this embodiment shown in FIG. 25 a full metallic plate corresponds to a given 4 bit word (e.g. 1111 or 0000) whereas in other adapters voids can be provided, e.g. by drilling holes in one or more of the positions facing the inductive sensors 1431 to give a different bit word for identification.

Figure 29:
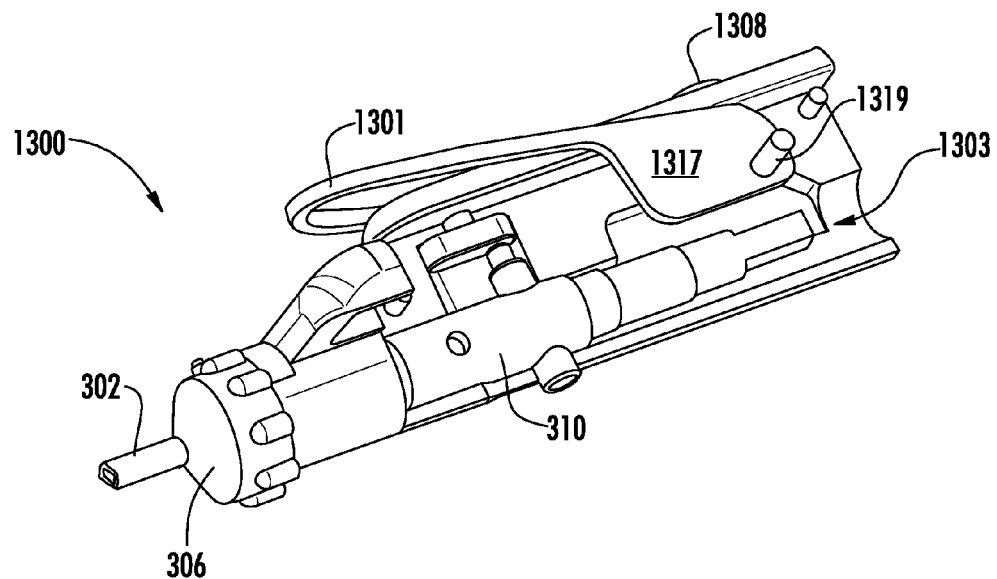
FIG. 29: is a partially broken perspective view of the ISA shown in FIG. 26 and FIG. 28.

FIG. 29 shows the ISA 1300 of FIG. 28 in partly dismantled view. As seen in FIG. 29, the ISA 1300 has an internal hollow serving as a cylindrical guide 1312 for a piston 310 of a certain manual laparoscopic instrument. The piston 310 is typically used in the manual instrument for communicating motion from the instrument handle to the shaft guided in the stem 302. It will be appreciated that the existing piston of a manual instrument can be arranged to slide in the guide 1312. As seen in FIG. 28, an oblong through hole 1315 is provided in the case 1303 allowing the slider pin 314 attached transversely to the piston 310 to protrude from the case 1303 and to be shifted forward and backward in axial direction of the case 1303 for operating the piston 310. The piston 310 shown in FIG. 29 is an original part of a manual bipolar instrument, used to provide bipolar electric power to the instrument and to lock/unlock the instrument.

Figure 30:
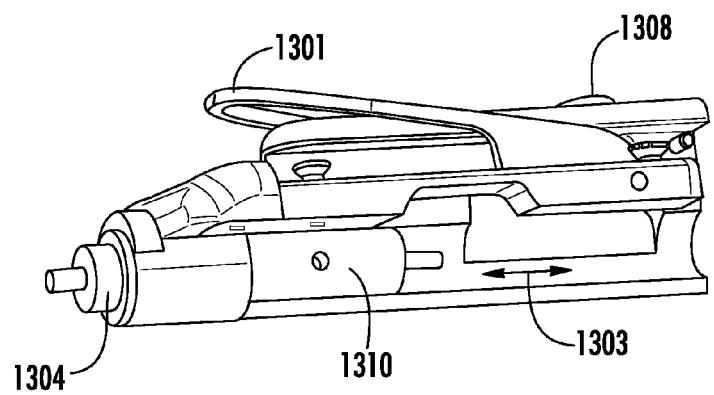
FIG. 30: is another partially broken perspective view of the ISA shown in FIG. 26 and FIG. 28 with different instrument connected to the adaptor.

FIG. 30 is to illustrate that the same type of adaptor can be used to accommodate different pistons of different types of commercially available laparoscopic instruments for manual intervention, e.g. the piston 1310 for a monopolar manual instrument as shown in FIG. 30. It follows that the adaptors such as the ISA 1300 (or ISA 300) allow using the essential parts of any commercially available relatively inexpensive manual instrument on the robot manipulator 14. FIG. 29 also shows one of the two tenons 1317 of the lever 1301 and the shaft 1319 on which it pivots. By pushing down the lever 1301, the tenons 1317 lift the lower surface, and in particular the ferromagnetic elements 1311, of the ISA 1300 away from the access surface 1401 of the ISA 1120 such that the ISA 1300 can be manually removed in a direction perpendicular to the axis of rotation of J6 i.e. the instrument stem axis.

In addition to the aspects described herein above, the robotic surgical system 10 further presents the following features:

the robot manipulators 14, by virtue of their design, can be easily and quickly retracted to permit the surgeon S to access the operation table 12 or to permit installation of a radiological instrument;

the robot manipulators 14, by virtue of their design and using information from an external sensor, can easily adapt with no significant increase of intervention time to angular variations of the operation table 12 during the intervention, for the (anti-) Trendelenburg (−/+20-35 deg.) or for sideways orientation of the patient;

the robot manipulators 14, by virtue of their design and using information from an external sensor, can easily manage trocar position variations due to changes of the intra-abdominal pressure;

the robotic surgical system 10 enables short instrument change times in order to minimize total intervention time, the design of the LIA 120; 1120 and the robot manipulator 14 enable instrument change times essentially as short as in manual laparoscopy procedures (ranging from 6 to 9 seconds), when used with an endoscope, the design of the robot manipulator 14 also enables quick endoscope extraction and reinsertion, e.g. for cleaning the optics;

the robotic surgical system 10 enables rapid and simple set-up of the system, including the configuration of a plurality of robot manipulators 14 around the operation table 12;

the robot manipulator 14 is designed versatile in order to be suitable for a variety of applications like minimally invasive surgery, orthopaedic, biopsy, percutaneous therapy, skin harvesting, ultra-sound diagnostics, etc.

While the present patent application as filed in principle concerns the invention as defined in the claims attached hereto, the person skilled in the art will readily understand that the present patent application contains support for the definition of other inventions, which could e.g. be claimed as subject matter of amended claims in the present application or as subject matter of claims in divisional and/or continuation applications. Such subject matter could be defined by any feature or combination of features disclosed herein.

The invention claimed is:

1. Robotic surgical system for performing minimally invasive medical procedures comprising a robot manipulator for robotically assisted handling of a laparoscopic instrument, said robot manipulator having a manipulator arm, a manipulator wrist supported by said manipulator arm and an effector unit supported by said manipulator wrist, wherein:

said manipulator arm provides three degrees-of-freedom by means of a first joint, a second joint and a third joint, each having an associated actuator, for robotically positioning said wrist;

said manipulator wrist provides two degrees-of-freedom by means of a fourth joint and a fifth joint, said fourth and fifth joints being revolute joints and each having an associated actuator, for robotically setting a yaw angle and a pitch angle of said effector unit respectively;

said effector unit comprises a laparoscopic instrument actuator and provides one degree-of-freedom by means of a revolute sixth joint having an associated actuator for robotically setting a roll angle of said laparoscopic instrument actuator;

said laparoscopic instrument actuator comprises a seat, with an associated coupling mechanism for mounting an instrument stem adaptor to said effector unit, and an actuation mechanism cooperating with said instrument stem adaptor for actuating a laparoscopic instrument connected to said adaptor;

said effector unit is configured such that the rotation axis of said revolute sixth joint coincides with the longitudinal axis of a laparoscopic instrument when mounted to said effector unit by means of said instrument stem adaptor; and said effector unit comprises a sensor assembly including a six degree-of-freedom force/torque sensor and a six degree-of-freedom accelerometer, said sensor assembly connecting said laparoscopic instrument actuator to said sixth revolute joint;

wherein said seat comprises an elongated essentially semi-cylindrical recess arranged essentially coaxial to the rotation axis of said sixth joint, in an access surface of said laparoscopic instrument actuator, said seat and said coupling mechanism being configured for mounting removing an instrument stem adaptor perpendicularly to the axis of rotation of said sixth joint.

2. Robotic surgical system according to claim 1, wherein said effector unit is configured such that one sensor axis of said 6 DOF force/torque sensor and one sensor axis of said 6 DOF accelerometer coincide with the rotation axis of said sixth joint.

3. Robotic surgical system according to claim 2, wherein said laparoscopic instrument actuator comprises a housing with an access surface in which said seat is arranged, an interface flange which attaches said housing to said sensor assembly and gradual reinforcing ribs connecting said access surface to said interface flange for reinforcing the rigidity of attachment of said housing to said interface flange.

4. Robotic surgical system according to claim 3, wherein said housing is semi-cylindrical having a semi-cylindrical surface opposite to said access surface, said semi-cylindrical surface being in conformity with a cylindrical envelope of 50-135 mm and coaxial to the rotation axis of said sixth joint and wherein said housing, said flange, said reinforcing ribs and said sensor assembly are dimensioned so as to fit into said cylindrical envelope.

5. Robotic surgical system according to claim 1, wherein said coupling mechanism comprises at least one magnetic device, in particular permanent magnets or electromagnets, respectively arranged on either side of said semi-cylindrical recess for fastening the instrument stem adaptor to said laparoscopic instrument actuator by means of magnetic attraction.

6. Robotic surgical system according to claim 5, wherein said instrument stem adaptor is mounted to the laparoscopic instrument actuator and configured to resist a plurality of forces and moments without disconnecting from the laparoscopic instrument actuator, said plurality of forces and moments including, a plurality of traction and compression forces of 100 N; a plurality of torsion moments corresponding to radial forces of 15 N at an instrument tip; and a bending moment of 5 Nm or less.

7. Robotic surgical system according to claim 1, wherein said actuation mechanism comprises a slider carriage configured for engagingly receiving and for linearly sliding a slider pin of the instrument stem adaptor mounted to said effector unit, said seat being preferably elongated along the rotation axis of said sixth joint and said slider carriage preferably arranged laterally to said seat.

8. Robotic surgical system according to claim 7, wherein said actuation mechanism comprises a force sensor, which connects said slider carriage to a driving means, for measuring forces exerted by or onto said slider carriage.

9. Robotic surgical system according to claim 7, wherein said slider carriage comprises an engagement member which is detachable from said slider carriage and has bevelled capture surfaces for engaging said slider pin.

10. Robotic surgical system according to claim 1, wherein said laparoscopic instrument actuator comprises a presence detector for detecting whether an instrument stem adaptor is correctly mounted to said effector unit, in particular, a plurality of inductive presence sensors for identifying an instrument mounted to said effector unit by means of an inductively identifiable pattern provided on the instrument stem adaptor.

11. Robotic surgical system according to claim 1, wherein said system is configured for operating in a manual mode, in which said laparoscopic instrument actuator can be positioned and oriented by said robot manipulator using information read by said 6 DOF force/torque sensor, and further comprising switching means arranged on said laparoscopic instrument actuator for switching said system to manual mode.

12. Laparoscopic instrument stem adaptor configured to be mounted to a robot manipulator in a new Robotic surgical system according to claim 1, for using a stem of the manual laparoscopic instrument on said robot manipulator, said adaptor comprising an elongated case having a stem connector arranged on a front end and coupling means arranged laterally on said case, said stem connector being configured for detachable connection to the manual laparoscopic instrument stem, and said coupling means cooperating with the coupling mechanism on the laparoscopic instrument actuator of said robot manipulator.

13. Laparoscopic instrument stem adaptor according to claim 12, wherein said coupling means comprises a semi-cylindrical surface, said surface being conformed to a semi-cylindrical recess of the seat in the laparoscopic instrument actuator of said robot manipulator for centering the instrument stem adaptor on the rotation axis of said sixth joint.

14. Laparoscopic instrument stem adaptor according to claim 12, comprising an internal cylindrical hollow as a guide for a piston of the manual laparoscopic instrument, which can be arranged to slide in said guide, and a through hole for a slider pin attached transversely to said piston and protruding from said case for operating the piston.

15. Laparoscopic instrument stem adaptor according to claim 12, wherein said coupling means comprises at least one ferromagnetic element arranged on either side of said case, said ferromagnetic elements cooperating respectively with a corresponding magnetic device of the coupling mechanism on said laparoscopic instrument actuator for fastening said instrument stem adaptor to said laparoscopic instrument actuator by means of magnetic attraction and wherein said instrument stem adaptor comprises a lever for detaching said adaptor from said laparoscopic instrument actuator.

16. Laparoscopic instrument stem adaptor according to claim 12, further comprising an inductively identifiable pattern provided on the instrument stem adaptor for identifying an instrument mounted to said adaptor.

17. Laparoscopic instrument stem adaptor according to claim 12, further comprising an electrical connector arranged opposite to said coupling means for transmitting electric power to an instrument connected to said stem connector.

18. Robotic surgical system according to claim 1, wherein the position of the effector unit with respect to the rotation axis of said fifth joint is selected at an equilibrium point of the effector unit configured to avoid tilting when said fifth joint is stopped and not powered.

19. A robot manipulator for robotically assisted handling of a laparoscopic instrument, said robot manipulator comprising a manipulator arm, a manipulator wrist supported by said manipulator arm and an effector unit supported by said manipulator wrist, said manipulator arm providing three degrees-of-freedom by means of a first joint, a second joint and a third joint, each having an associated actuator, for positioning said wrist;

said manipulator wrist providing two degrees-of-freedom by means of a fourth joint and a fifth joint, said fourth and fifth joints being revolute joints and each having an associated actuator, for setting a yaw angle and a pitch angle of said effector unit respectively;

said effector unit comprising a laparoscopic instrument actuator and provides one degree-of-freedom by means of a revolute sixth joint having an associated actuator for setting a roll angle of said laparoscopic instrument actuator;

said laparoscopic instrument actuator comprising a seat and an associated coupling mechanism for mounting an instrument stem adaptor to said effector unit;

said effector unit being configured such that the rotation axis of said revolute sixth joint coincides with the longitudinal axis of a laparoscopic instrument when mounted to said effector unit by means of said instrument stem adaptor; and said effector unit comprising a sensor assembly including a six degree-of-freedom force/torque sensor and a six degree-of-freedom accelerometer, said sensor assembly connecting said laparoscopic instrument actuator to said sixth revolute joint;

wherein said seat comprises an elongated essentially semi-cylindrical recess arranged, essentially coaxial to the rotation axis of said sixth joint, in an access surface of said laparoscopic instrument actuator, said seat and said coupling mechanism being configured for mounting and removing an instrument stem adaptor perpendicularly to the axis of rotation of said sixth joint.

20. Robot manipulator according to claim 19, wherein said effector unit is configured such that one sensor axis of said 6 DOF force/torque sensor and one sensor axis of said 6 DOF accelerometer coincide with the rotation axis of said sixth joint.

21. Robot manipulator according to claim 19, wherein said laparoscopic instrument actuator comprises a housing with an access surface in which said seat is arranged, an interface flange which attaches said housing to said sensor assembly and gradual reinforcing ribs connecting said access surface to said interface flange for reinforcing the rigidity of attachment of said housing to said interface flange.

22. Robot manipulator according to claim 21, wherein said housing is semi-cylindrical having a semi-cylindrical surface opposite to said access surface, said semi-cylindrical surface being in conformity with a cylindrical envelope, preferably of 50-135 mm, and coaxial to the rotation axis of said sixth joint and wherein said housing, said flange, said reinforcing ribs and said sensor assembly are dimensioned so as to fit into said cylindrical envelope.

23. Robot manipulator according to claim 19, wherein said coupling mechanism comprises at least one magnetic device, in particular permanent magnets and/or electromagnets for fastening an instrument stem adaptor to said laparoscopic instrument actuator by means of magnetic attraction.

24. Robot manipulator according claim 19, wherein said laparoscopic instrument actuator comprises an actuation mechanism cooperating with said instrument stem adaptor for actuating the laparoscopic instrument connected to said adaptor, said actuation mechanism comprising a slider carriage configured for engagingly receiving and for linearly sliding a slider pin of an instrument stem adaptor mounted to said effector unit, said seat being preferably elongated along the rotation axis of said sixth joint and said slider carriage preferably arranged laterally to said seat and said actuation mechanism further comprising a force sensor, which connects said slider carriage to a driving means, for measuring forces exerted by or onto said slider carriage.

25. Robot manipulator according to claim 19, wherein said laparoscopic instrument actuator comprises a presence detector for detecting whether an instrument stem adaptor is correctly mounted to said effector unit, in particular, a plurality of inductive presence sensors for identifying an instrument mounted to said effector unit by means of an inductively identifiable pattern provided on the instrument stem adaptor.

* * * * *